United States Patent [19]

Paoletti et al.

[11] Patent Number: 4,769,330

[45] Date of Patent: Sep. 6, 1988

[54] MODIFIED VACCINIA VIRUS AND METHODS FOR MAKING AND USING THE SAME

[75] Inventors: Enzo Paoletti, Delmar; Dennis Panicali, Averill Park, both of N.Y.

[73] Assignee: Health Research, Incorporated, Albany, N.Y.

[21] Appl. No.: 334,456

[22] Filed: Dec. 24, 1981

[51] Int. Cl.$^4$ .................. C12N 15/00; C12N 7/00; C12N 7/04; C12N 5/00; C12P 21/00; C12P 19/34; C12R 1/91

[52] U.S. Cl. .................. 435/172.3; 435/68; 435/91; 435/172.1; 435/235; 435/236; 435/240.1; 435/240.2; 435/948; 935/32; 935/57

[58] Field of Search .................. 435/172, 68, 317, 194, 435/948, 172.3, 70, 240, 241, 235, 236, 91, 320, 172.1; 935/32, 57

[56] References Cited

PUBLICATIONS

Morse et al: J. Virol. 26, 389 (1978).
Mocarski et al: Cell 22, 243 (1980).
Post et al., Cell 25 (1981) 227-2333.
Bossart et al., Chem. Abstr. 89 (1978) 56251 n.
Katz et al., Chem. Abstr. 89 (1978) 39241 s.
Smiley, Nature 285 (1980) 333-335.
Comparative Diagnosis of Viral Diseases, vol. III, Ch. 6, p. 277, Academic Press, New York, 1981.
Comprehensive Virology, Fraenkel-Conrad et al., vol. 3, Ch. 5, pp. 405, 427, Plenum Press, New York.
Virology, Dulbecco et al., Ch. 56, pp. 1079 and 1082-1085, Harper & Row, Hagerstown.
Baxby, Progr. med. Virol. 19 (1975) 215-246.
Downie et al., Ann. Rev. Microbiol. 10 (1956) 237-252.
Woodroofe et al., Virology 12 (1960) 272-282.
Woodroofe et al., Virology 16 (1962) 334-341.
Müller et al., J. gen. Virol. 38 (1977) 135-147.
Mackett et al., J. gen. Virol. 45 (1979) 683-701.
Fenner, Virology 5 (1958) 502-529.
Fenner, Virology 8 (1959) 499-507.
Joklik, Bacteriological Reviews 30 (1966) 33-66.
Wittek et al., J. Virol. 23 (1977) 669-678.
Hamer et al., Nature 281, 35-40 (1979).
Sveda et al., Proc. Natl. Acad. Sci. USA 78, 5488-5492 (1981).
Sarver et al., Moc. Cell. Biol. 1, 486-496 (1981).
Panicali et al., J. Virol 37, 1000-1010 (1981).
Shimotohno et al., Cell 26, 66-77 (1981).
Sam et al., Ann. Virol. 132 E, 135-150 (1981).
Colbere-Garapin, Prod. Natl. Acad. Sci. USA 76, 3755-3759 (1979).
Wigler et al. Cell 11, 223-232 (1977).
Graham et al., Virology 52, 456-467 (1973).
Wigler et al., Proc. Natl. Acad. Sci. USA 76, 1373-1376 (1979).
Villarreal et al., Science 196, 183-185 (1977).
Campione-Piccardo et al., J. Virol 31, 281-287 (1979).
Bolivar et al. Gene 2, 95-113 (1977).

*Primary Examiner*—James Martinell
*Attorney, Agent, or Firm*—Curtis, Morris & Safford

[57] ABSTRACT

What are disclosed are methods for modifying the genome of vaccinia virus to produce vaccinia mutants, particularly by the introduction into the vaccinia genome of exogenous DNA; modified vaccinia prepared by such methods; certain DNA sequences and unmodified and genetically modified microorganisms involved as intermediates in such methods; and methods for infecting cells and host animals with such vaccinia mutants to provoke the amplification of exogenous DNA and proteins encoded by the exogenous DNA, including antigenic proteins, by said cells and host animals.

19 Claims, 4 Drawing Sheets

FIG. 1

FIG. 2

| GENE | GROWTH IN NORMAL MEDIUM? | GROWTH IN HAT MEDIUM? | GROWTH IN BUdR? |
|---|---|---|---|
| TK⁺ | YES | YES | NO |
| TK⁻ | YES | NO | YES |

MODIFIED VACCINIA VIRUS AND METHODS FOR MAKING AND USING THE SAME

The invention described herein was made with the support of the Federal Government and the Federal Government has certain rights in the invention.

The present invention relates to modified vaccinia virus, to methods of making and using the same, and to other modified and unmodified microorganisms, and to certain DNA sequences, produced or involved as intermediates in the production of modified vaccinia virus. More in particular, the invention relates to vaccinia virus in which the naturally occurring genome of the virus has been altered ("vaccinia mutants") and to methods of making and using such vaccinia mutants, as well as to other unmodified and genetically modified microorganisms, and to certain DNA sequences, produced or involved as intermediates in the production of vaccinia mutants.

Vaccinia virus is the prototypic virus of the pox virus family and, like other members of the pox virus group, is distinguished by its large size and complexity. The DNA of vaccinia virus is similarly large and complex. Vaccinia DNA is about 120 megadaltons in size, for instance, compared with a DNA size of only 3.6 megadaltons for simian virus 40 (SV40). The DNA molecule of vaccinia is double-stranded and terminally cross-linked so that a single stranded circle is formed upon denaturation of the DNA. Vaccinia DNA has been physically mapped using a number of different restriction enzymes and a number of such maps are presented in an article by Panicali et al., J. Virol. 37, 1000–1010 (1981) which reports the existence of two major DNA variants of the WR strain of vaccinia virus (ATCC No. VR 119) which strain has been most widely used for the investigation and characterization of pox viruses. The two variants differ in that the S("small") variant (ATCC No. VR 2034) has a 6.3 megadalton deletion not occurring in the DNA of the L("large") variant (ATCC No. VR 2035). Maps obtained by treatment of the variants with the restriction enzymes Hind III, Ava I, Xho I, Sst I, and Sma I are presented in the aforementioned article.

Vaccinia, a eukaryotic virus, reproduces entirely within the cytoplasm of a host cell. It is a lytic virus, i.e. a virus, the replication of which in a cell results in lysis of the cell. The virus is considered non-oncogenic. The virus has been used for approximately 200 years in vaccines for inoculation against smallpox and the medical profession is well acquainted with the properties of the virus when used in a vaccine. Although inoculation with vaccinia is not without risk, the risks are on the whole well known and well defined and the virus is considered relatively benign.

At the heart of the present invention is the modification of the naturally occurring vaccinia genome to produce vaccinia mutants by rearrangement of the natural genome, by the removal of DNA from the genome, and/or by the introduction into the naturally occurring vaccinia genome of DNA which disrupts the naturally occurring genome ("foreign DNA"). Such foreign DNA may be naturally occurring in vaccinia or may be synthetic or may be naturally occurring in an organism other than vaccinia. If genetic information is present in this foreign DNA, the potential exists for the introduction of this information into a eukaryote via modified vaccinia virus. That is, the modified virus represents a relatively innocuous eukaryotic cloning vector from which genetic information has been deleted, or into which information has been inserted or in which genetic information has been rearranged. Since the virus replicates within the cytoplasm of an infected cell modified vaccinia virus represents a unique eukaryotic cloning vector unlike any other so far considered or currently under investigation.

This discovery has a number of useful consequences, among which are (A) novel methods for vaccinating mammals susceptible to vaccinia to induce in them an antibody response to antigens coded for by foreign DNA inserted into the vaccinia virus, (B) novel methods for the production by eukaryotic cells of biological products other than antigens, and (C) novel methods for the introduction into human or animal individuals or populations of missing genes or of genetic material for the modification, replacement, or repair of defective genes in the individuals or populations.

Suitably modified vaccinia mutants carrying exogenous genes which are expressed in a host as an antigenic determinant eliciting the production by the host of antibodies to the antigen represent novel vaccines which avoid the drawbacks of conventional vaccines employing killed or attenuated live organisms. Thus, for instance the production of vaccines from killed organisms requires the growth of large quantities of the organisms followed by a treatment which will selectively destroy their infectivity without affecting their antigenicity. On the other hand, vaccines containing attenuated live organisms always present the possibility of a reversion of the attenuated organism to a pathogenic state. In contrast, when a modified vaccinia mutant suitably modified with a gene coding for an antigenic determinant of a disease-producing organism is used as a vaccine, the possibility of reversion to a pathogenic organism is avoided since the vaccinia virus contains only the gene coding for the antigenic determinant of the disease producing organism and not those genetic portions of the organism responsible for the replication of the pathogen.

The present invention offers advantages even with respect to new technology employing genetic engineering involving the production of an antigen by a recombinant prokaryotic organism containing a plasmid expressing a foreign antigenic protein. For instance, such technology requires the production of large amounts of the recombinant prokaryotic cells and subsequent purification of the antigenic protein produced thereby. In contrast, a modified vaccinia virus used for innoculation according to the present invention replicates within the innoculated individual to be immunized thereby amplifying the antigenic determinant in vivo.

A further advantage of the use of vaccinia mutants as vectors in eukaryotic cells as vaccines or for producing biological products other than antigens is the possibility for post-translational modifications of proteins produced by the transcription of exogenous genes introduced into the cell by the virus. Such post-translational modifications, for instance glycosylation of proteins, are not likely in a prokaryotic system, but are possible in eukaryotic cells where additional enzymes necessary for such modifications are available. A further advantage of the use of vaccinia mutants for inoculation is the possibility of amplification of the antibody response by the incorporation, into the mutant, of tandem repeats of the gene for the antigen or of additional genetic elements which stimulate the immune response, or by the use of a strong promoter in the modified virus. A similar advantage holds in the production of biological products other than antigens.

Returning to a more detailed consideration of the vaccinia genome, the cross-linked double strands of the DNA are characterized by inverted terminal repeats each approximately 8.6 megadaltons in length, representing about 10 kilobasepairs (kbp). Since the central portions of the DNA of all pox viruses are similar, while the terminal portions of the viruses differ more strongly, the responsibility of the central portion for functions common to all the viruses, such as replication, is suggested, whereas the terminal portions appear responsible for other characteristics such as pathogenicity, host range, etc. If such a genome is to be modified by the rearrangement or removal of DNA fragments therefrom or the introduction of exogenous DNA fragments thereinto, while producing a stable viable mutant, it is evident that the portion of the naturally-occurring DNA which is rearranged, removed, or disrupted by the introduction of exogenous DNA thereinto must be non-essential to the viability and stability of the host, in this case the vaccinia virus. Such non-essential portions of the genome have been found to be present in the WR strain of vaccinia virus, for instance within the region present within the L-variant but deleted from the S-variant or within the Hind III F-fragment of the genome.

The modification of vaccinia virus by the incorporation of exogenous genetic information can be illustrated by the modification of the WR strain of vaccinia virus in the Hind III F-fragment thereof to incorporate into that fragment a gene of herpes simplex virus type I (HSV) responsible for the production of thymidine kinase (TK). TK is an enzyme which phosphorylates the nucleoside thymidine to form the corresponding monophosphorylated nucleotide which is subsequently incorporated into DNA.

The HSV TK gene represents DNA foreign to vaccinia virus which is convenient to introduce into vaccinia according to the present invention for a number of reasons. First, the gene is relatively readily available present in a herpes simplex virus DNA fragment that is produced by digestion with Bam HI endonuclease, as reported by Colbere-Garapin et al. in Proc. Natl. Acad. Sci. USA 76, 3755-3759 (1979). Second, this HSV Bam HI fragment has been introduced into plasmids and into eukaryotic systems in the prior art, for instance as reported by Colbere-Garapin et al., loc. cit. and by Wigler et al., Cell 11, 223-232 (1977). Third, experience has shown that if HSV TK can be introduced as an exogenous gene into a eukaryotic system, and is expressed—which requires unambiguous and faithful translation and transcription of the genetic locus—, then other exogenous genes can similarly be introduced and expressed.

BRIEF DESCRIPTION OF THE DRAWINGS

A better understanding of the present invention will be had by referring to the accompanying drawings, in which FIG. 1 is a map of the aforementioned L- and S-variants of the WR strain of vaccinia determined using Hind III as a restriction enzyme and showing the deletion of sequences in the terminal C fragment of the L-variant, which deletion is outside the terminal repeat section of the genome. The deleted DNA sequences are unique to the L structure and, since the growth of the S- and L-variants is identical, this deleted region must be non-essential;

FIG. 2 shows the vaccinia Hind III F-fragment in greater detail including two further restriction sites therein, namely Sst I and Bam HI, at least the latter of which sites offers a locus at which exogenous DNA can be introduced into the vaccinia Hind III F-fragment without disturbing any essential vaccinia genes;

FIGS. 3 A-C schematically show a method for the introduction of the HSV TK gene into the vaccinia Hind III F-fragment;

FIG. 4 is a restriction map of certain vaccinia mutants produced according to the present invention and shows in detail the position of the HSV TK inserts present in the Hind III F-fragment in two such virus mutants, designated herein as VP-1 and VP-2;

FIG. 5 is a table summarizing certain techniques useful in screening possible recombinant viruses to determine the presence or absence of the HSV TK gene therein; and FIGS. 6 A-C are restriction maps of the left-hand terminal portion of the vaccinia WR genome showing the relationship of various restriction fragments to the unique L-variant DNA sequence deleted from the corresponding S-variant.

Referring to FIG. 1, if the L- and S-variants of the vaccinia virus are subjected to the action of Hind III, a restriction enzyme well known in the prior art and commercially available, the virus genomes are respectively cleaved into 15 or 14 segments designated with the letters A through O, with the letter A used to designate the largest fragment and the letter O used to designate the smallest. The electrophoretic separation of the restriction fragments is described and shown in the aforementioned publication of Panicali et al., J. Virol. 37, 1000-1010 (1981). The F-fragment obtained in this manner from either the L- or S-variants has a molecular weight of 8.6 megadaltons. The position of the F-fragment is shown on the restriction map presented as FIG. 1 accompanying the application and a restriction map of the F-fragment is shown in FIG. 2. The restriction enzyme Hind III recognizes the nucleotide sequence —AAGCTT— and cleaves the DNA between the adjacent adenosine groups to give fragments having "sticky ends" with the sequence AGCT—. Since larger quantities of the Hind III F-fragment of vaccinia than are readily obtainable by restriction of the vaccinia genome are required for manipulation according to the present invention, the F-fragment is inserted into a plasmid cloning vector for purposes of amplification.

Namely, the vaccinia Hind III F-fragment produced in this manner is conveniently introduced into the plasmid pBR 322 which is cut only once by a number of restriction enzymes, including Hind III. The pBR 322 plasmid was first described by Bolivar et al. in Gene 2, 95-113 (1977) and is now commercially available within the United States from a number of sources.

The location of the Hind III cleavage site on the pBR 322 plasmid is indicated in FIG. 3A relative to cleavage sites of Eco RI and Bam HI, which are other restriction enzymes. If the pBR 322 plasmid is cut with Hind III and the resultant cleaved DNA is mixed with vaccinia Hind III F-fragment, and if the fragments are ligated with $T_4$ DNA ligase, as suggested in FIG. 3A, the F-fragment is incorporated into the plasmid to produce the novel plasmid pDP 3 shown schematically in FIG. 3B and having a molecular weight of approximately 11.3 megadaltons. The vaccinia Hind III F-fragment includes approximately 13 kilobasepairs in comparison with the 4.5 kilobasepairs found in the pBR 322 portion of pDP 3. T$_4$ DNA ligase is a commercially available enzyme and the conditions for its use in the manner indicated are well known in the art.

The pDP 3 plasmid is now introduced into a microorganism such as *Escherichia coli* (*E. coli*) by transformation for purposes of replicating the Hind III F-fragment for recovery of larger quantities of the F-fragment. These techniques of cleaving a plasmid to produce linear DNA having ligatable termini and then inserting exogenous DNA having complementary termini in order to produce a replicon (in this case the pBR 322 containing vaccinia Hind III F-fragment) are known in the art, as is the insertion of the replicon into a microorganism by transformation (cf. U.S. Pat. No. 4,237,224).

Unmodified pBR 322 plasmid confers ampicillin resistance (Amp ®) and tetracycline resistance (Tet ®) to its host microorganism, in this case *E. coli*. However, since Hind III cuts the pBR 322 plasmid in the Tet ® gene, the introduction of the vaccinia Hind III F-fragment destroys the Tet ® gene and tetracycline resistance is lost. Hence, the *E. coli* transformants containing the pDP 3 plasmid can be distinguished from untransformed *E. coli* by the simultaneous presence of resistance to ampicillin and susceptibility to tetracycline. It is these *E. coli* transformed with pDP 3 which are grown in large quantities and from which large quantities of the pDP 3 are recovered.

The conditions under which plasmids can be amplified in *E. coli* are well known in the art, for example from the paper of Clewel, J. Bacteriol. 110, 667-676 (1972). The techniques of isolating the amplified plasmid from the *E. coli* host are also well known in the art and are described, for instance, by Clewel et al. in Proc. Natl. Acad. Sci. USA 62, 1159-1166 (1969).

In a similar fashion, the pBR 322 plasmid can be conveniently cleaved by treatment with the restriction enzyme Bam HI and a modified plasmid can be prepared by the insertion thereinto of a Bam HSV TK fragment, all as discussed in the aforementioned work of Colbere-Garapin et al., loc. cit. The modified plasmid containing the Bam HI fragment which includes the HSV TK gene can again be introduced into *E. coli* by known methods and the transformed bacteria grown for amplification of the plasmid in large quantities. The amplified Bam HSV TK-pBR 322 recombinant plasmid is subsequently cleaved with Bam HI to isolate the Bam HI fragment containing the HSV TK gene using the same prior art techniques mentioned earlier with regard to the amplification of the Hind III F-fragment of vaccinia.

Figures 1, 2:
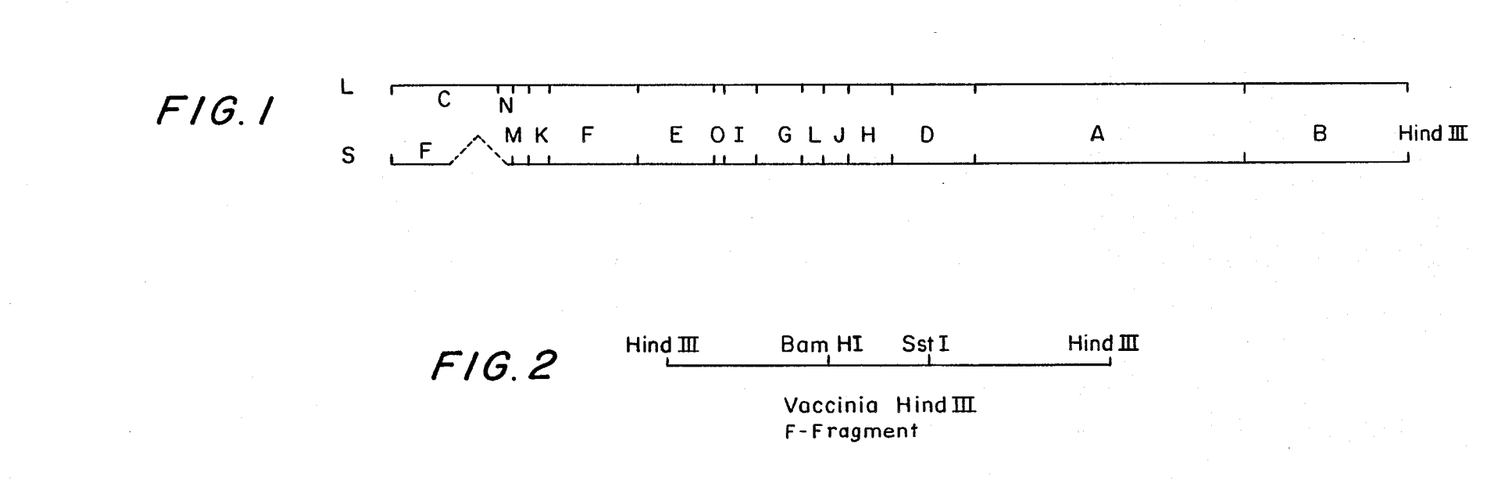
Figure 3A:
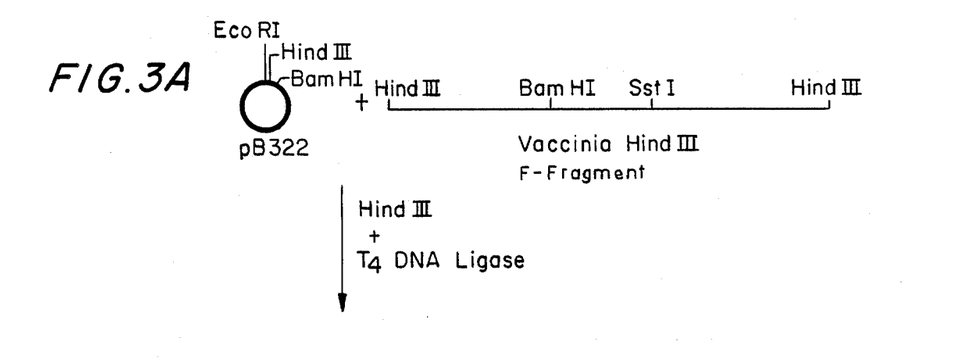
Figure 3B:
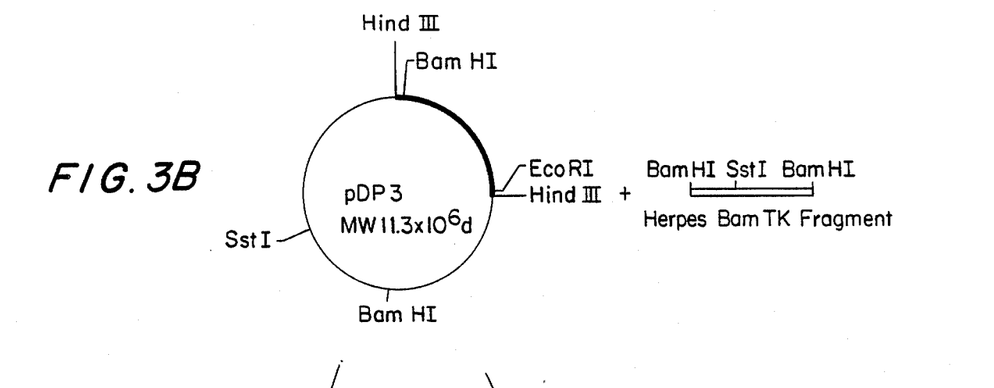

To construct a recombinant plasmid having the Bam HI HSV TK fragment included within the vaccinia Hind III F-fragment, the pDP 3 plasmid is next subjected to a partial restriction with Bam HI such that only one of the two Bam HI cleavage sites within the plasmid is cleaved, i.e. either that Bam HI site within the Hind III F-fragment or the Bam HI site within the pBR 322 portion of the pDP 3 plasmid, as shown in FIG. 3B. The cleaved, now-linear, DNA is then combined with purified Bam HSV TK fragment. The linear segments are combined and ligated by treatment with T$_4$ DNA ligase, again using techniques known in the art.

The combination of the Bam HSV TK fragment with the cleaved pDP 3 plasmid is a random or statistical event leading to the possible production of numerous species formed by various combinations of the fragments present in the mixture, all of which have identical "sticky ends". Thus, one possibility is the simple rejoining of the Bam HI cleaved ends of the pDP 3 plasmid to reform the circular plasmid. Another possibility is the joinder of two or more Bam HSV TK fragments in either of two orientations. Further, the Bam HSV TK fragment (or a multiple thereof) may be combined with the linear DNA of a pDP 3 plasmid which has been cleaved at the Bam HI site within the pBR 322 portion, again in either of two orientations, or one or more Bam HSV TK fragments may be combined, again in either of two orientations, with linear pDP 3 DNA which has been cleaved at the Bam HI site within the vaccinia Hind III F-fragment portion of the pDP 3 plasmid.

To permit the identification and separation of these various possibilities, the products of ligation are inserted into a unicellular microorganism such as *E. coli* by techniques like those described earlier and known in the art. The *E. coli* thus treated are then grown on a medium containing ampicillin. Those bacteria which contain any plasmid are ampicillin resistant because all such plasmids contain that gene of pBR 322 which confers ampicillin resistance. Hence, all surviving bacteria are transformants which are then screened further to determine the presence or absence of the Bam HSV TK fragment possibly present.

To accomplish this, those bacteria containing any TK gene are identified by hybridization with radio-labelled TK DNA. If the TK gene is present in the bacterium the radio-labelled TK DNA will hybridize with that portion of the plasmid present in the bacterium. Since the hybrid is radioactive, the colonies containing TK within their plasmids can be determined by means of autoradiography. The bacteria containing TK can in turn be grown. Finally, then, bacteria containing plasmids having the TK incorporated within the pBR 322 portion can be identified and separated from those having the TK fragment in the vaccinia Hind III F-fragment by analysis with restriction endonucleases.

More in detail, the bacteria surviving growth on nutrient agar plates containing ampicillin are partially transferred to a nitrocellulose filter by contact of the filter with the plate. The bacteria remaining on the plate are regrown and the bacteria which have been transferred to the nitrocellulose filter to create a replica of the original plate are next treated to denature their DNA. Denaturation is effected, for example, by treatment of the transferred bacteria with sodium hydroxide followed by neutralization and washing. Subsequently, the now-denatured DNA present on the nitrocellulose filter is hybridized by treatment with HSV Bam TK containing radioactive $^{32}$P. The nitrocellulose filter so treated is next exposed to X-ray film which darkens in those portions in which hybridization with the radio-labelled Bam HSV TK has taken place. The exposed darkened X-ray film is next compared with the original plate and those colonies growing on the original plate corresponding to the colonies causing darkening of the X-ray film are identified as those containing a plasmid in which Bam HSV TK is present.

Finally, to discriminate between those bacteria containing a plasmid in which the Bam HSV TK gene has been incorporated within the pBR 322 portion of the plasmid from those wherein Bam HSV TK is present in the F-fragment of the plasmid, small cultures of the bacteria are grown and the plasmids are isolated therefrom by a mini-lysis technique known in the art and described in the paper of Holmes et al., Anal. Bioch. 114

193-197 (1981). The plasmids are next digested with the restriction enzyme Hind III which cleaves the circular plasmid at the two points of original joinder of the F-fragment with the pBR 322 DNA chain. The molecular weight of the digestion product is next determined by electrophoresis on agarose gels with the distance of migration in the gels being a measur of the molecular weight.

If the Bam HSV TK fragment or a multiple thereof is found in the F-segment of the digested plasmid, the gel will show the presence of the pBR 322 fragment plus a second fragment having a molecular weight greater than that of the F-fragment by the molecular weight of the Bam HSV TK DNA segment or segments included therein. Conversely, if the Bam HSV TK is present in the pBR 322, electrophoresis will show the presence of an F-fragment of the usual molecular weight plus a further fragment larger than pBR 322 by the molecular weight of the Bam HSV TK fragment or fragments present therein. Those bacteria in which modification with Bam HSV TK has occurred in the pBR 322 portion of the plasmid are discarded: the remaining bacteria have been modified in the F-fragment portion of the plasmid therein. It is these plasmids which are used for incorporation of the Bam HSV TK fragment into vaccinia.

As mentioned earlier, the combination of the DNA fragments to regenerate a plasmid is a random event according to which a number of which different plasmid structures having Bam HSV TK in the F-fragment can result.

To determine the orientation of the Bam HSV TK fragment within the F-fragment, as well as the number of such Bam HSV TK fragments possibly present, the plasmids are recovered from each of those bacterial colonies which are known to have an Bam HSV TK fragment present in the F-fragment of the plasmid. The mini-lysis technique mentioned earlier herein is used for this purpose. The plasmids are then again subjected to restriction analysis, this time using the commercially available restriction enzyme Sst I. Since each Bam HSV TK fragment has an Sst I restriction site therein, and since the F-fragment of vaccinia similarly has a single Sst I restriction site therein (cf. the representation of these fragments in FIGS. 3A and 3B respectively), different numbers of fragments of differing molecular weights can be detected by electrophoresis on agarose gels, the number and molecular weight of the segments being dependent on the orientation of the Bam HSV TK fragment within the F-fragment and the number of such Bam TK fragments present. Orientation of the Bam TK fragment within the F-fragment can be detected because of the asymmetry of the Bam HSV TK fragment with respect to the Sst I site therein (cf. FIG. 3B).

For instance, in the particular experiments under discussion, six bacterial colonies each having one or more Bam HSV TK fragments present in the F-fragment of the plasmid were found among the E. coli transformants. After restriction analysis of the plasmids in these bacteria along the lines discussed above, two of the recombinant plasmids were chosen for further study because the direction of orientation of the Bam HSV TK fragment within the F-fragment was in opposite directions.

At this point, the reader is reminded that the introduction of the HSV TK gene into the F-fragment of vaccinia, as discussed in detail above, is merely exemplary of one of many possible means of modifying the vaccinia genome to produce desirable vaccinia mutants. Thus, the introduction of the same exogenous gene into another portion of the vaccinia genome, or the introduction of different genetic material into the vaccinia F-fragment or into some other fragment, all may require modification of the exemplary scheme, discussed above, for the identification of recombinant organisms.

Figure 6A:
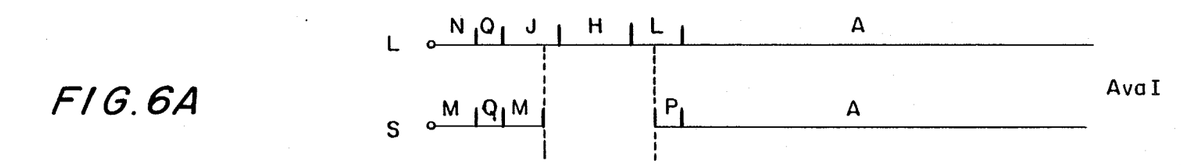

For instance, digestion of the vaccinia L-variant with Ava I yields a fragment, H, entirely with the region deleted from the S-variant (cf. FIG. 6 A and the discussion thereof infra). This H-fragment contains Bam HI sites permitting the introduction thereinto of the HSV TK gene. The same scheme for identifying F-fragment-HSV TK recombinants can be used for identifying such H-fragment recombinants also.

Indeed, schemes for the construction and identification of F-fragment-HSV TK recombinants, alternative to that disclosed in detail above by way of illustration, do exist. For instance, the Bam HI site in pBR 322 can be removed by cleavage of the plasmid with Bam HI and treatment with DNA polymerase I to "fill in" the "sticky ends". This product is then cut with Hind III and the linear fragment is treated with alkaline phosphatase to prevent recircularization of the plasmid upon ligation. However foreign DNA, and particularly the vaccinia Hind III F-fragment, can be ligated to the treated pBR 322 and the resulting plasmid will recircularize. Now, treatment with Bam HI effects cleavage of the plasmid only within the vaccinia F-fragment portion thereof. Subsequent treatment of the cleavage product with alkaline phosphatase an ligation with the Bam HI HSV TK fragment will produce recombinants with high efficiency s that the recombinants can be screened by restriction endonuclease cleavage and gel electrophoresis. This technique eliminates the time-consuming steps of discriminating between recombinants having HSV TK in the pBR 322 portion or in the F-fragment and colony hybridization.

Figure 3C:
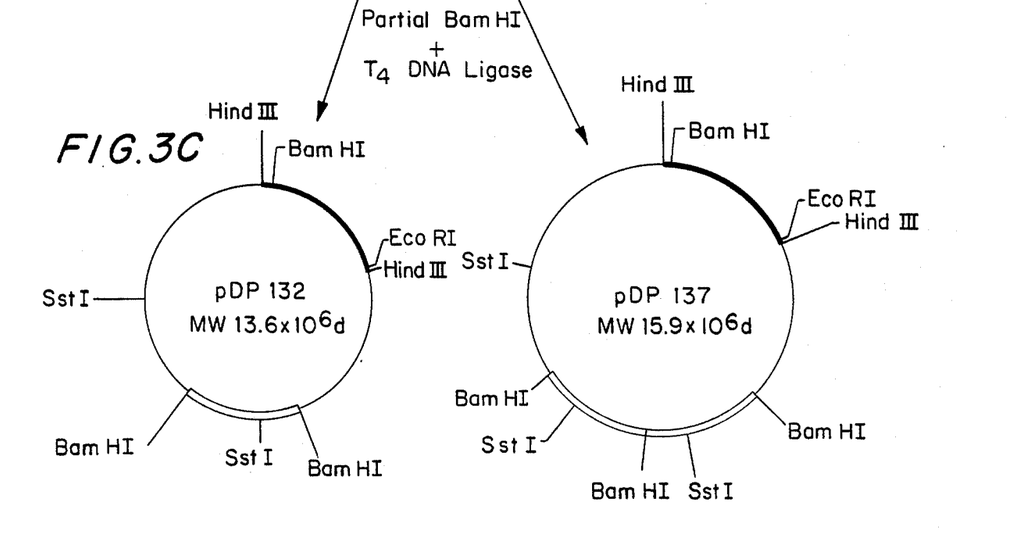

Returning now to further discussion of the plasmids produced in the exemplary mutation of vaccinia by the introduction of HSV TK into the vaccinia F-fragment the two recombinant plasmids chosen for further study are shown in FIG. 3C, where they are identified as a first novel plasmid, pDP 132, incorporating one Bam HSV TK fragment within the vaccinia Hind III F-portion, and a second novel plasmid, pDP 137, in which two Bam HSV TK fragments joined "head to tail" have been incorporated. The single fragment of Bam HSV TK has been incorporated within pDP 132 in the opposite sense in which two Bam TK fragments have been included in tande in pDP 137. Namely, the region of the TK gene within the Bam HI fragment which codes for the 5'-end of mRNA produced by the gene is located between the Sst I cleavage site and the nearer of the two Bam HI sites thereto (again cf. FIG. 3B). The direction of transcription of the HSV TK gene on the Bam TK fragment proceeds from the 5'-end to the 3'-end and will be in a clockwise direction in pDP 132 as shown in FIG. 3C. [cf. Smiley et al., Virology 102, 83–93 (1980)]. Conversely, since the Bam TK fragments included in tandem in pDP 137 have been incorporated in the reverse sense, transcription of the HSV TK genes contained therein will be in the opposite direction, namely in a counter-clockwise direction. The direction of inclusion of the Bam HSV TK fragment within the vaccinia Hind III F-fragment may be of importance in case promotion of transcription of the HSV TK gene is initiated by a promoter site within the F-fragment itself. However, HSV promoter sites do exist within the Bam HSV TK fragment itself, so that transcription of the HSV TK gene may occur no matter in which direction the Bam HSV TK fragment and HSV TK gene have been incorporated within the vaccinia Hind III F-fragment.

Those *E. coli* transformants containing pDP 132 or pDP 137 are next grown to produce large amounts of the plasmids for further processing. When a sufficient amount of the plasmid DNA has been isolated, restriction with Hind III yields a modified vaccinia Hind III F-fragment having the HSV TK gene therein. This modified Hind III F-fragment is now introduced into vaccinia virus by novel methods, described below in greater detail, in order to produce an infectious entity.

To review the prior art, at present the vector principally used for introducing exogenous DNA into eukaryotic cells is SV40. The DNA of SV40 is circular and can be treated much like a plasmid. That is, the circular DNA is cleaved with a restriction enzyme, combined with exogenous DNA, and ligated. The modified DNA can be introduced into eukaryotic cells, for instance animal cells, by standard techniques [cf. Hamer et al., Nature 281, 35-40 (1979)]. The DNA is infectious and will replicate in the nucleus of the cell producing viable mutated viruses. In contrast, vaccinia replicates within the cytoplasm of a eukaryotic cell. The purified DNA of this virus is not infectious and cannot be used per se to produce vaccinia mutants in a cell in the same manner as SV40. Rather novel techniques involving the mutation of wild type vaccinia with foreign DNA in vivo within a cell must be employed.

An unpublished paper of the applicants together with Eileen Nakano, reports a demonstration of marker rescue in vaccinia virus. According to these experiments, that portion of the L-variant DNA which is normally absent from the S-variant can be reintroduced into the S-variant ("rescued") under appropriate conditions. Namely, eukaryotic cells ar treated with live infectious S-variant vaccinia virus together with non-infectious restriction fragments of the DNA of the L-variant, representing DNA "foreign" to the S-variant, of a particular structure. Namely, that portion of the L-variant DNA which is to be rescued must be present within a DNA chain having portions co-linear with the DNA chain of the S-fragment into which it is to be introduced. That is, the "foreign" DNA to be introduced into the S-variant has at both ends of the DNA chain, a region of DNA which is homologous with corresponding sequences in the S-variant. These homologous sequences can be viewed as "arms" attached to the region of L-variant DNA which is to be rescued by the S-variant.

The mechanism of this recombination is complex and has not yet been accomplished in vitro. Apparently, the recombination of the L-DNA into the S-variant involves homologous base pairing in segments surrounding the area deleted from the S-variant. Most likely, cross-overs from one strand of DNA to another result in an in vivo recombination of the DNA to rescue the deleted portion.

This technique of in vivo recombination can be used to introduce foreign DNA other than vaccinia DNA into either the S- or the L-variant of vaccinia. Thus, the modified Hind III F-fragment incorporating the Bam HSV TK fragment therein as DNA "foreign" to vaccinia can be introduced into vaccinia by treating eukaryotic cells with the modified F-fragment together with infectious L- and/or infectious S-variants of vaccinia virus. In this instance, the portions of the F-fragment flanking the Bam HSV TK fragment function as the "arms" mentioned earlier comprising DNA homologous with DNA present in the L- or S-variant into which the modified F-fragment is to be introduced. Again, by in vivo processes within the cell, the mechanisms of which are not known in detail, the HSV TK-modified F-fragment is incorporated into the vaccinia variants in the cell and is then capable of replication and expression under vaccinia control.

This in vivo recombination technique is broadly applicable to the introduction of still other "foreign" DNA into vaccinia, providing a pathway by which the genome of vaccinia can be modified to incorporate a wide variety of foreign genetic material thereinto, whether such foreign DNA be derived from vaccinia itself, be synthetic, or be derived from organisms other than vaccinia.

A wide variety of cells can be used as the host cells in which the in vivo recombination described above takes place. The recombination, however, occurs with differing efficiency depending on the cell employed. Of the cells investigated to date, baby Syrian hamster kidney cells [BHK-21 (Clone 13) (ATCC No. CCL10)] have proved most efficient for the recombination procedure. However, other cells including CV-1 (ATCC No. CCL70), a green monkey kidney cell line, and human (line 143) TK-cells, a 5'-BUdR resistant mutant derived from human cell line R970-5, have also been infected in this manner to generate vaccinia mutants.

These cells are suitably treated with vaccinia an the foreign DNA to be incorporated into the vaccinia while, for convenience, the cells are in the form of a monolayer. For purposes of in vivo recombination, the cells may be infected with vaccinia followed by treatment with the foreign DNA to be incorporated thereinto, or may first be contacted with the foreign DNA followed by infection with vaccinia. As a third alternative, the vaccinia and foreign DNA may be simultaneously present at the time the cells are treated.

The viruses are suitably contacted with the cell monolayer while present in a conventional liquid medium, such as phosphate buffered saline, Hepes buffered saline, Eagle's Special medium (with or without serum addition), etc. which is compatible with these cells and the viruses.

The foreign DNA is conveniently used to treat these cells while in the form of a calcium phosphate precipitate. Such techniques for introducing DNA into cells have been described in the prior art by Graham et al., Virology 52, 456-467 (1973). Modifications of the technique have been discussed by Stow et al., J. Gen. Virol. 33, 447-458 (1976) and Wigler et al., Proc. Natl. Acad. Sci. USA 76, 1373-1376 (1979). The treatments taught in these papers conveniently proceed at room temperature but temperature conditions can be varied within limits preserving cell viability, as can the time for which the cells are treated with the virus and/or foreign DNA precipitate, with various efficiencies of the in vivo recombination. The concentration of the infecting vaccinia virus and the amount of foreign DNA precipitate employed will also affect the rate or degree of recombination. Other factors such as atmosphere and the like are all chosen with a view to preserving cell viability. Otherwise, as long as the three necessary components (cell, virus, and DNA) are present, in vivo recombination will proceed at least to some extent. Optimization of the conditions in a particular case is well within the capabilities of one skilled in the microbiological arts.

Following this recombination step, those vaccinia viruses which have been mutated by in vivo recombination must be identified and separated from unmodified vaccinia virus.

Vaccinia viruses mutated by in vivo recombination of foreign DNA thereinto can be separated from unmodified vaccinia virus by at least two methods which are independent of the nature of the foreign DNA or the ability of the mutant to express any gene which may be present in the foreign DNA. Thus, first, the foreign DNA in the mutant genome can be detected by restriction analysis of the genome to detect the presence of a extra piece of DNA in the mutated organism. In this method individual viruses isolated from purified plaques are grown and the DNA is extracted therefrom and subjected to restriction analysis using appropriate restriction enzymes. Again, by detecting the number and molecular weight of the fragments determined, the structure of the genome prior to restriction can be deduced. However, because of the necessity of growing purified plaques, the number of analyses which must be made, and the possibility that none of the plaques grown and analyzed will contain a mutant, this technique is laborious, time consuming and uncertain.

Further, the presence of foreign DNA in vaccinia virus can be determined using a modification of the technique taught by Villarreal et al. in Science 196, 183–185 (1977). Infectious virus is transferred from viral plaques present on an infected cell monolayer to a nitrocellulose filter. Conveniently, a mirror-image replica of the transferred virus present on the nitrocellulose filters is made by contacting a second such filter with that side of the first nitrocellulose filter to which the viruses have been transferred. A portion of the viruses present on the first filter is transferred to the second filter. One or the other of the filters, generally the first filter, is now used for hybridization. The remaining filter is reserved for recovery of recombinant virus therefrom once the locus of the recombinant virus has been detected using the hybridization technique practiced on the companion, mirror-image filter.

For purposes of hybridization, the viruses present on the nitrocellulose filter are denatured with sodium hydroxide in a manner known per se. The denatured genetic material is now hybridized with a radio-labelled counterpart of the gene whose presence is sought to be determined. For example, to detect the possible presence of vaccinia mutants containing the Bam HSV TK fragment, the corresponding radio-labelled Bam HSV TK fragment containing $^{32}P$ is employed, much in the same manner as discussed earlier herein with respect to the detection of plasmids modified by the presence of this fragment. Non-hybridized DNA is washed from the nitrocellulose filter and the remaining hybridized DNA, which is radioactive, is located by autoradiography, i.e. by contacting the filter with X-ray film. Once the mutated viruses are identified, the corresponding virus plaques present on the second filter, containing a mirror image of the viruses transferred to the first filter, are located and grown for purposes of replicating the mutated viruses.

The two methods described above involve a analysis of the genotype of the organism involved and, as mentioned earlier, can be used whether or not any gene present within the foreign DNA incorporated into the vaccinia virus is expressed. However, if the foreign DNA is expressed, then phenotypic analysis can be employed for the detection of mutants. For example, if the gene is expressed by the production of a protein to which an antibody exists, the mutants can be detected by a method employing the formation of antigen-antibody complexes. See Bieberfeld et al. J. Immunol. Methods 6, 249–259 (1975). That is, plaques of the viruses including the suspected mutants are treated with the antibody to the protein which is produced by the mutan vaccinia genotype. Excess antibody is washed from the plaques, which are then treated with protein A labelled with $^{125}I$. Protein A has the ability of binding to the heavy chains of antibodies, and hence will specifically label the antigen-antibody complexes remaining on the cell monolayer. After excess radioactive protein A is removed, the monolayers are again picked up by plaque lifts onto nitrocellulose filters and are subjected to autoradiography to detect the presence of the radio-labelled immune complexes. In this way, the mutated vaccinia viruses producing the antigenic protein can be identified.

In the specific instance in which the foreign DNA includes the HSV TK gene, once it is known that the mutated vaccinia virus expresses the HSV TK gene therein, a much simpler and elegant means for detecting the presence of the gene exists. Indeed, the ease of discrimination between vaccinia mutants containing the HSV TK gene and unmodified vaccinia free of this gene provides a powerful tool for discriminating between vaccinia virus mutants containing other exogenous genes either present alone in the vaccinia genome or present therein in combination with the HSV TK gene. These methods are described more in detail later herein.

Since eukaryotic cells have their own TK gene and vaccinia virus similarly has its own TK gene (utilized, as noted above, for the incorporation of thymidine into DNA), the presence and expression of these genes must be in some way distinguished from the presence and expression of the HSV TK gene in vaccinia mutants of the type under discussion. To do this, use is made of the fact that the HSV TK gene will phosphorlyate halogenated deoxycytidine, specifically iododeoxycytidine (IDC), a nucleoside, but neither the TK gene of vaccinia nor the TK gene of cells will effect such a phosphorylation. When IDC is incorporated into the DNA of a cell it becomes insoluble. Non-incorporated IDC, on the other hand, is readily washed out from cell cultures with an aqueous medium such as physiologic buffer. Use is made of these facts as follows to detect the expression of the HSV TK gene in vaccinia mutants.

Namely, cell monolayers are infected with mutated virus under conditions promoting plaque formation, i.e. those promoting cell growth and virus replication. When the cells are infected, they are then treated with commercially available radio-labelled IDC (IDC*), labelling being easily effected with $^{125}I$. If the cells are infected with a virus containing the HSV TK gene, and if the HSV TK gene present therein is expressed, the cell will incorporate IDC* into its DNA. If the cell monolayers are now washed with a physiologic buffer, non-incorporated IDC* will wash out. If the cell monolayers are next transferred to a nitrocellulose filter and exposed to X-ray film, darkening of the film indicates the presence of IDC* in the plaques an demonstrates the expression of the HSV TK gene by the vaccinia mutants.

Using the aforementioned genotypic and phenotypic analyses the applicants have identified two vaccinia mutants denominated VP-1 and VP-2. VP-1 (ATCC No. VR 2032) is a recombinant vaccinia virus derived from vaccinia S-variant modified by in vivo recombination with the plasmid pDP 132. VP-2 (ATCC No. VR 2030) is an S-variant vaccinia virus modified by recombination with pD 137.

Figure 4A:
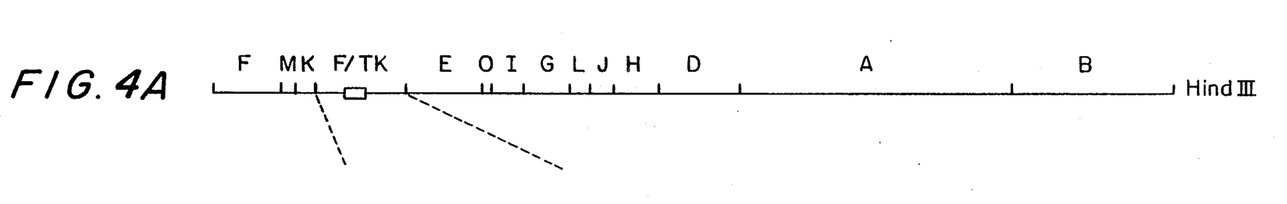
Figure 4B:
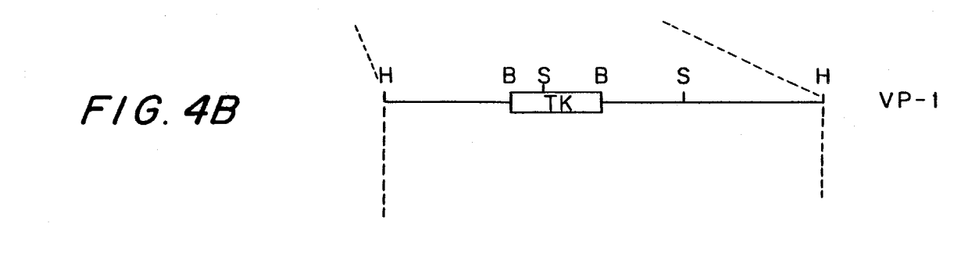
Figure 4C:
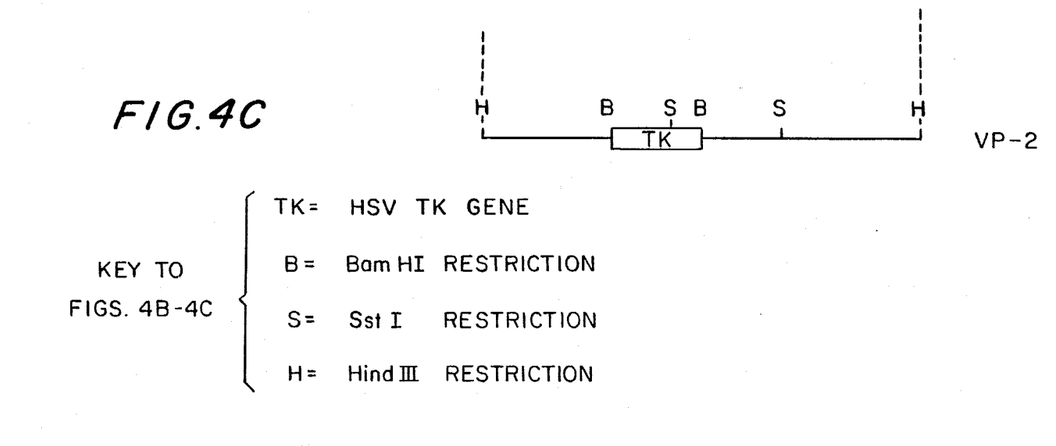

FIG. 4A is a Hind III restriction map of the vaccinia genome showing the site of the HSV TK gene insertion. FIGS. 4B and 4C magnify the Hind III F-fragment respectively contained in VP-1 and VP-2 to show the orientation of the Bam HI HSV TK fragment therein. Attention is called to the fact that the in vivo recombination of pDP 137 with the S-variant (i.e. VP-2) effects deletion of one of the Bam HI HSV TK fragments present in tandem in the starting plasmid.

As mentioned earlier, the fact that the HSV TK gene is expressed can be used for a rapid and easy detection and identification of mutants which contain or are free of HSV TK gene or of a foreign gene present alone or in combination with the HSV gene. The test and its bases are described immediately below.

The applicants have isolated in biologically pure form, a vaccinia mutant, an S-variant in particular, which is free of any naturally-occurring functional TK gene, denominated VTK−79 (ATTC No. VR 2031). Normally, the S- and L-variants discussed earlier herein have a TK gene in the Hind III fragment J thereof. If this mutant, free of vaccinia TK gene activity, is used for the production of further mutated organisms containing the HSV TK gene, incorporated into the vaccinia mutant by the techniques described earlier herein, the HSV TK gene present in such resultant mutants will be the only functional TK gene present in the virus. The presence or absence of such an HSV TK gene can be immediately detected by growing cells infected with the viruses on one of several selective media.

Namely, one such selective medium contains bromodeoxyuridine (BUdR), a nucleoside analogous to thymidine, but highly mutagenic and poisonous to organisms such as a cell or virus when present in DNA contained therein. Such a medium is known from Kit et al., Exp. Cell Res. 31, 297–312 (1963). Other selective media are the hypoxanthine/aminopterin/thymidine (HAT) medium of Littlefield, Proc. Natl. Acad. Sci. USA 50, 568–573 (1963) and variants thereof such as MTAGG described by Davis et al., J. Virol. 13, 140–145 (1974) or the further variant of MTAGG described by Campione-Piccardo et al. in J. Virol. 31, 281–287 (1979). All these media selectively discriminate between organisms containing and expressing a TK gene and those which do not contain or express any TK gene. The selectivity of the media is based on the following phenomena.

There are two metabolic pathways for the phosphorylation of thymidine. The primary metabolic pathway does not rely upon thymidine kinase and, while it synthesizes phosphorylated thymidine by intermediate mechanisms, it will not phosphorylate BUdR or directly phosphorylate thymidine The secondary metabolic pathway does involve the activity of thymidine kinase and will result in the phosphorylation of both thymidine and its analog, BUdR. Since BUdR is a poisonous highly mutagenic substance, the presence of TK, such as the HSV TK under discussion, in an organism will result in the phosphorylation of BUdR and its incorporation into the DNA of the growing organism, resulting in its death. On the other hand, if the TK gene is absent or not expressed, and the primary metabolic pathway which then is followed results in the synthesis of phosphorylated thymidine but not in the phosphyorylation of BUdR, the metabolizing organism will survive in the presence of BUdR since this substance is not incorporated into its DNA.

Figure 5:
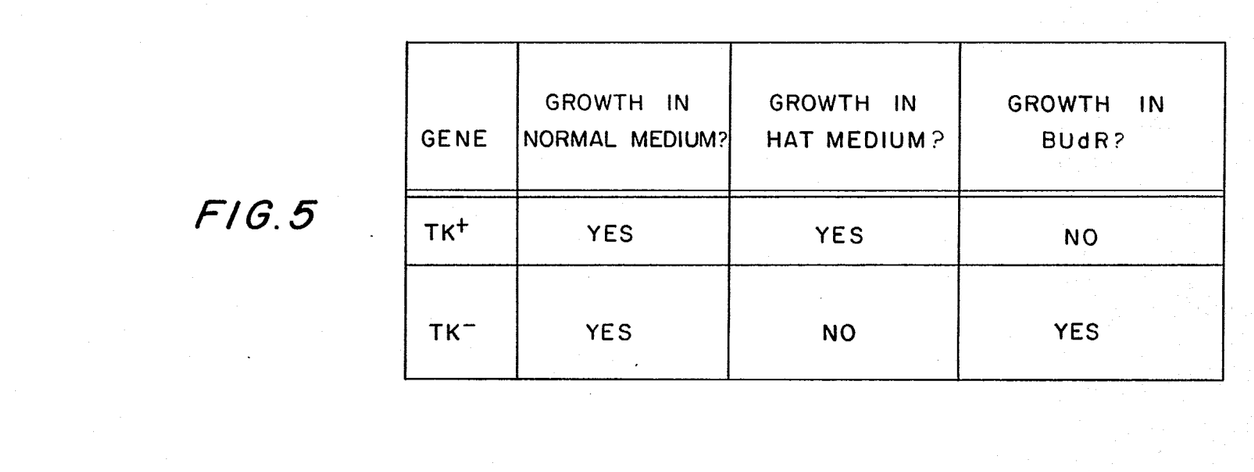

The growth behaviors discussed above are summarized in FIG. 5 of the accompanying drawings tabulating the growth behavior or organisms expressing TK (TK+) and organisms free of or not expressing the TK gene (TK−) on a normal medium, on a selective medium such as HAT which blocks the primary metabolic pathway not using TK, and on a medium containing BUdR. TK+ and TK− organisms will both grow on a normal growth medium by employing the primary metabolic pathway not requiring TK. On a selective medium such as HAT which blocks the primary metabolic pathway not relying on TK, the TK+ organism will nevertheless grow because the enzyme accomplishes the phosphorylation necessary for incorporation of thymidine into DNA. On the other hand, the TK− organisms will not survive. In contrast, if the organisms are grown on a medium containing BUdR, the TK+ variants will die since TK phosphorylates BUdR and this poisonous material is incorporated in the DNA. In contrast, since BUdR is not phosphorylated by the primary metabolic pathway, the TK− variant will grow since BUdR is not incorporated into the DNA.

Thus, if a vaccinia virus free of vaccinia TK, such as VTK−79, is used as the vaccinia virus into which the HSV TK gene is inserted by the techniques of the present invention, the presence and expression, or the absence, of the HSV TK gene therein can be readily determined by simply growing the recombinants on a selective medium such as HAT. Those viruses which are mutated will survive since they use the HSV TK to synthesize DNA.

The applicants have indeed prepared several mutants of vaccinia virus free of vaccinia TK. These have been denominated VP-3 (ATCC No. VR 2036), a recombinant of VTK−79 and pDP 132, and VP-4 (ATCC No. VR 2033), a recombinant of VTK−79 and pDP 137. The latter expresses the HSV gene and can readily be identified using the selective media mentioned above.

Two additional recombinant viruses, denominated VP-5 (ATCC No. VR 2028), and VP-6 (ATCC No. VR 2029), are respectively recombinants of pDP 132 and pDP 137 with VTK−11 (ATCC No. VR 2027), a known L-variant of vaccinia which does not express the vaccinia TK gene. Thus, DNA can be introduced in excess of the maximum vaccinia genome length.

The techniques of the present invention can be used to introduce the HSV TK gene into various portions of the vaccinia genome for purposes of identifying non-essential portions of the genome. That is, if the HSV TK gene can be inserted into the vaccinia genome, as it is in the Hind III F-fragment thereof, the region of the genome into which it has been introduced is evidently non-essential. Each non-essential site within the genome is a likely candidate for the insertion of exogenous genes so that the methods of the present invention are useful in mapping such non-essential sites in the vaccinia genome.

Further if the HSV TK gene is coupled with another exogenous gene and the resultant combined DNA material is put into a vaccinia virus free of vaccinia TK gene, such as VTK−79, recombinants which are formed and which contain the foreign gene will express the HSV TK gene and can be readily separated from the TK− variants by the screening technique described immediately above

A further embodiment of the invention involves the preparation of a vaccinia Hind III F-fragment containing an exogenous gene therein and the treatment of cells with the fragment together with a vaccinia mutant not expressing the vaccinia TK gene but having the HSV TK gene incorporated therein by in vivo recombination according to the techniques of the present invention. As with the marker rescue mentioned earlier herein and the in vivo techniques employed to incorporate the TK- modified Hind III F-fragment into vaccinia, cross-over and recombination can occur to produce a further mutant in which the HSV T modified F-fragment is replaced by an F-fragment containing another exogenous gene. The resulting vaccinia mutant, in which the HSV TK F-fragment has been replaced by a F-fragment containing the exogenous gene, will be totally free of TK, whereas the non-mutated parent virus predominantly present will still be HSV TK+. Similarly a foreign gene may be inserted into the HSV TK gene present in such a vaccinia mutant, disrupting the integrity of the gene rendering the recombinant organism TK- in comparison with the non-mutated TK+ parent. In both instances, an immediate discrimination can be made between those vaccinia mutants containing the foreign gene and those which are free of any TK by growth on BUdR and/or a special medium such as HAT.

A better understanding of the present invention and of its many advantages will be had by referring to the following specific Examples, given by way of illustration. The percentages given are percent by weight unless otherwise indicated.

EXAMPLE I

Isolation of Vaccinia Hind III Fragments from Agarose Gels

Restriction endonuclease Hind III was purchased from Boehringer Mannheim Corp. Preparative digestions of DNA were performed in 0.6 ml of Hind III buffer containing 10 millimolar (mM) Tris-HCl (pH 7.6), 50 mM NaCl, 10 mM $MgCl_2$, 14 mM dithiothreitol (DTT), and 10 micrograms ($\mu g$)/ml of bovine serum albumin (BSA) in which are present 10–20 $\mu g$ of vaccinia DNA and 20–40 units of Hind III (1 unit is the amount of enzyme sufficient to cleave 1 ug of lambda-DNA completely in 30 minutes.)

Vaccinia DNA was extracted and purified from virions as follows. Purified virions were lysed at a concentration having an optical density per ml of 50 measured at 260 nanometers ($A_{260}$) in 10 mM Tris-HCl (pH 7.8), 50 mM beta-mercaptoethanol, 100 mM NaCl, 10 mM $Na_3EDTA$, 1% Sarkosyl NL-97, and 26% sucrose. Proteinase K was added to 100 $\mu g$/ml and the lysate incubated at 37° C. overnight. DNA was extracted by the addition of an equal volume of phenol-chloroform (1:1). The organic phase was removed and the aqueous phase reextracted until the interface was clear. Two additional extractions with chloroform were performed and the aqueous phase was then dialyzed extensively against 10 mM Tris-HCl (pH 7.4) containing 0.1 mM Na EDTA at 4° C. DNA was concentrated to approximately 100 $\mu g$/ml with Ficoll (a synthetic high copolymer of sucrose and epichlorohydrin).

Digestion of the DNA was for 4 hours at 37° C. The reactions were terminated by heating to 65° C. for 10 minutes followed by addition of an aqueous stop solution containing 2.5% of agarose, 40% of glycerol, 5% of sodium dodecyl sulfate (SDS), and 0.25% of bromophenol blue (BPB). Samples were layered at 65° C. onto agarose gel and allowed to harden prior to electrophoresis.

Electrophoresis was carried out in 0.8% agarose gels (0.3×14.5×30 cm) in electrophoresis buffer containing 36 mM Tris-HCl (pH 7.8), 30 mM $NaH_2PO_4$, and 1 mM EDTA. Electrophoresis was at 4° C. for 42 hours at 50 volts. The gels were stained with ethidium bromide (1 $\mu g$/ml in electrophoresis buffer). The restriction fragments were visualized with ultraviolet (UV) light and individual fragments were cut from the gel.

Fragments were separated from the agarose gel according to the procedure of Vogelstein et al., Proc. Natl. Acad. Sci. USA 76, 615–619 (1979) using glass powder as follows. The agarose gel containing a DNA fragment was dissolved in 2.0 ml of a saturated aqueous solution of NaI. 10 mg of glass powder were added per $\mu g$ of DNA calculated to be present. The solution was rotated at 25° C. overnight to bind the DNA to the glass powder. The DNA-glass powder was collected by centrifugation at 2000 rpm for 5 minutes. The DNA-glass was then washed with 5 ml of 70% NaI. The DNA-glass was again collected by centrifugation and washed in a mixture of 50% buffer [20 mM Tris-HCl (pH 7.2), 200 mM NaCl, 2 mM EDTA] and 50% ethanol. The DNA-glass was collected again by centrifugation and was gently suspended in 0.5 ml of 20 mM Tris-HCl (pH 7.2), 200 mM NaCl, and 2 mM EDTA. The DNA was then eluted from the glass powder at 37° C. by incubation for 30 minutes. The glass was then removed by centrifugation at 10,000 rpm for 15 minutes. DNA was recovered from the supernatant by ethanol precipitation and dissolved in 10 mM Tris-HCl (pH 7.2) containing 1 mM EDTA.

The F-fragment isolated in this way was used in the following Examples.

EXAMPLE II

Insertion of the Vaccinia Hind III-F Fragment Into the Hind III Site of pB 322 (Construction of pDP 3 [pBR 322-Vaccinia Hind III F-Recombinant Plasmid])

Vaccinia Hind III-F fragment was isolated from preparative agarose gels as described in Example I. This fragment was inserted into the Hind III site of pBR 322 [Bolivar et al., Gene, 2, 95–113 (1977)] as follows.

Approximately 200 nanograms (ng) of pBR 322 were cleaved with Hind III in 10 mM Tris-HCl (pH 7.6), 50 mM NaCl, 10 mM $MgCl_2$, and 14 mM DTT [Hind III buffer] using 1 unit of enzyme for 1 hour at 37° C. The reaction was stopped by heating to 65° C. for 10 minutes 500 ng of isolated Hind III vaccinia F-fragment were added and the DNAs co-precipitated with 2 volumes of ethanol at −70° C. for 30 minutes. The DNA was then washed with 70% aqueous ethanol, dried, and resuspended in ligation buffer consisting of 50 mM Tris-HCl (pH 7.6), 10 mM $MgCl_2$, 10 mM DTT, and 1 mM adenosine triphosphate (ATP). Approximately 100 units of $T_4$ DNA ligase (New England Biolabs) were then added and the mixture was incubated at 10° C. overnight. The ligase-treated DNA was then used to transform E. coli HB101 [Boyer et al., J. Mol. Biol. 41, 459–472 (1969)].

EXAMPLE III

Transformation of E. coli and Selection for Recombinant Plasmids

Competent cells were prepared and transformed with plasmids according to the procedure described by Dagert e al., Gene 6, 23-28 (1979). E. coli HB101 cells were made competent by inoculating 50 ml of LB broth (1% of bacto-tryptone, 0.5% of bacto-yeast extract, and 0.5% of NaCl supplemented with 0.2% of glucose) with 0.3 ml of an overnight culture of the cells and allowing them to grow at 37° C. until the culture had an optical density (absorbence), at 650 nanometers ($A_{650}$), of 0.2, as measured with a spectrophotometer. The cells were then chilled on ice for 10 minutes, pelleted by centrifugation, resuspended in 20 ml of cold 0.1 molar (M) $CaCl_2$, and incubated on ice for 20 minutes. The cells were then pelleted and resuspended in 0.5 ml of cold 0.1 M $CaCl_2$ and allowed to remain at 4° C. for 24 hours. The cells were transformed by adding ligated DNA (0.2-0.5 mg in 0.01-0.02 ml of ligation buffer) to competent cells (0.1 ml). The cells were then incubated on ice for 10 minutes and at 37° C. for 5 minutes. 2.0 ml of LB broth were then added to the cells and incubated at 37° C. for 1 hour with shaking. Aliquots of 10 microliters ($\mu l$) or 100 $\mu l$ were then spread on LB agar plates containing ampicillin (Amp) at a concentration of 100 ug/ml The transformed bacteria were then screened for recombinant plasmids by transferring ampicillin resistant ($Amp^R$) colonies to LB agar containing tetracycline (Tet) at 15 ug/ml. Those colonies which were both $Amp^R$ and tetracycline sensitive ($Tet^S$) (approximately 1%) were screened for intact vaccinia Hind III-F fragment inserted into pBR 322 according to the procedure of Holmes et al., Anal. Bioch. 114, 193-197 (1981). 2.0 ml cultures of transformed E. coli were grown overnight at 37° C. The bacteria were pelleted by centrifugation and resuspended in 105 ul of a solution of 8% sucrose, 5% Triton X-100, 50 mM EDTA, and 50 mM Tris-HCl (pH 8.0), followed by the addition of 7.5 $\mu l$ of a freshly prepared solution of lysozyme (Worthington Biochemicals) [10 mg/ml in 50 m Tris-HCl(pH 8.0)]. The lysates were placed in a boiling water bath for 1 minute and then centrifuged at 10,000 rpm for 15 minutes. The supernatant was removed and plasmid DNA precipitated with an equal volume of isopropanol. The plasmids were then resuspended in 40 $\mu l$ of Hind III buffer and digested with 1 unit of Hind III for 2 hours. The resulting digests were then analyzed on a 1.0% analytical agarose gel for the appropriate Hind III-F fragment. One such recombinant plasmid containing an intact Hind III-F fragment, denominated pDP 3, was used for further modification. (See FIG. 3B).

EXAMPLE IV

Preparative Isolation of pDP 3

Large scale isolation and purification of plasmid DNA was performed by a modification of the procedure of Clewel et al., Proc. Natl. Acad. Sci. USA 62, 1159-1166 (1969). 500 ml of LB broth were inoculated with 1.0 ml of an overnight culture of E. coli HB 101 containing pDP 3. At an optical density ($A_{600}$) of approximately 0.6, chloramphenicol was added (100 $\mu g/ml$) to amplify the production of plasmids [Clewel J. Bacteriol. 110, 667-676 (1972)]. The bacteria were incubated at 37° C. for an additional 12-16 hours at which time they were collected by centrifugation at 5000 rpm for 5 minutes, washed once in 100 ml of TEN buffer [0.1 mM Tris-HCl (pH 8.0), 150 mM NaCl, 10 mM EDTA], collected by centrifugation and resuspended in 14 ml of a 25% solution of sucrose in 0.05 M Tris-HCl (pH 8.0). 4.0 ml of lysozyme solution [5 mg/ml in 0.25 M Tris-HCl (pH 8.0)] were added and the mixture was incubated at room temperature for 30 minutes followed by the addition of 4.0 ml of 0.25 M EDTA (pH 8.0). The mixture was then put on ice for 10 minutes. 2.0 ml of pancreatic RNase A (Sigma Chemical Co.) [1 mg/ml in 0.25 M Tris-HCl (pH 8.0)] were added to this mixture, which is then incubated at room temperature for 1 minute. The cells were then lysed by adding 26 ml of a lytic Triton solution [1% Triton X-100, 0.05 M EDTA, 0.05 M Tris-HCl (pH 8.0)]. The mixture was incubated at room temperature for 30-60 minutes. The lysate was cleared by centrifugation at 17,000 rpm for 30 minutes at 4° C. The supernatant wa then removed and plasmid DNA separated from chromosomal DNA on dye-bouyant CsCl gradients.

For this purpose, CsCl-ethidium bromide gradients were prepared by dissolving 22 g of CsCl in 23.7 ml of cleared lysate. 1.125 ml of aqueous ethidium bromide (10 mg/ml) were added to the solution. The mixture was then centrifuged in polyallomer tubes in a Beckman 60 Ti rotor at 44,000 rpm for 48-72 hours. The resulting bands of DNA in the gradients were visualized with ultraviolet light and the lower band (covalently closed plasmid DNA) was removed by puncturing the tube with an 18 gauge needle attached to a syringe. Ethidium bromide was removed from the plasmid by repeated extraction with 2 volumes of chloroform-isoamyl alcohol (24:1). Plasmids were then dialyzed extensively against 10 mM Tris-HCl (pH 7.4) containing 0.1 mM EDTA to remove CsCl. The plasmid DNA was then concentrated by ethanol precipitation.

EXAMPLE V

Construction of pBR 322/Vaccinia/Herpes Virus TK Recombinant Plasmids

FIGS. 3B and 3C summarize the steps involved in the construction of the recombinant plasmids used for inserting the Bam HSV TK fragment into S- or L-variant vaccinia. Approximately 15 ug of covalently closed pDP 3 were cleaved by partial digestion with Bam HI (Bethesda Research Laboratories) by incubation in Bam HI buffer, consisting of 20 mM Tris-HCl (pH 8.0), 7 mM $MgCl_2$, 100 mM NaCl, and 2 mM beta-mercaptoethanol, using 7 units of Bam HI for 10 minutes at 37° C. Since pBR 322 and vaccinia Hind III F each contain a Bam HI site, partial cleavage results in a mixture of linear plasmids cut either at the pBR 322 or vaccinia Bam HI site. These mixed linear plasmids were then separated from the fragments of pDP 3 cut at both the pBR 322 and vaccinia Bam HI sites by electrophoresis on agaros gels and the singly cut linear plasmids were isolated using glass powder as described in Example I.

A recombinant pBR 322 containing the 2.3 megadalton (md) HSV Bam HI fragment which codes for HSV TK, as described by Colbere-Garapin et al., Proc. Natl. Acad. Sci. USA 76, 3755-3759 (1979), was digested to completion with Bam HI and the 2.3 md Bam TK fragment was isolated from an agarose gel as described above.

pDP 3 Bam TK recombinant plasmids were constructed by ligating approximately 1 $\mu g$ of Bam HI linearized pDP 3 to approximately 0.2 μg of isolated Bam TK fragment in 20 μl of ligation buffer containing 100 units of T4 DNA ligase at 10° C. overnight. This ligation mixture was then used to transform competent E. coli HB 101 cells as described in Example III.

EXAMPLE VI

Screening of Transformed Cells for Identification of Those Containing Recombinant Plasmids Having HSV TK Inserts Transformed cells containing recombinant plasmids were screened for HSV TK insertions by colony hybridization essentially as described by Hanahan et al., Gene 10, 63-67 (1980).

A first set of nitrocellulose filters (Schleiche and Schull BA85) were placed on Petri dishes filled with LB agar containing 100 μg/ml of ampicillin. Transformed cells were spread on the filters and the dishes were incubated at 30° C. overnight or until the colonies were just visible. A replica nitrocellulose filter of each of the first set of filters was made by placing a sterile nitrocellulose filter on top of each of the above-mentioned original filters and pressing the two filters together firmly. Each pair of filters was then notched (keyed) with a sterile scalpel blade, separated, and each filter was transferred to a fresh LB agar plate containing ampicillin at 100 μg/ml for 4-6 hours. The first set of filters (original filters) were then placed on LB agar plates containing 200 μg/ml of chloramphenicol to amplify plasmid production. The replica filters were stored at 4° C.

After 24 hours on chloramphenicol, the original nitrocellulose filters were prepared for hybridization as follows. Each nitrocellulose filter was placed on a sheet of Whatman filter paper saturated with 0.5 N NaOH for 5 minutes, blotted on dry filter paper for 3 minutes, and placed back on the NaOH saturated filter paper for 5 minutes to lyse the bacteria thereon and to denature their DNA. This sequence was then repeated using Whatman filter paper sheets saturated with 1.0 M Tris-HCl (pH 8.0) and repeated a third time with filter paper sheets saturated with 1.0 M Tris-HCl (pH 8.0) containing 1.5 M NaCl for purposes of neutralization. The nitrocellulose filters treated in this manner were then air dried and baked in vacuo at 80° C. for 2 hours.

Prior to hybridization these nitrocellulose filters were next treated for 6-18 hours by incubating at 60° C. in a prehybridization buffer which is an aqueous mixture of 6×SSC [1×SSC=0.15 M NaCl and 0.015 M Na citrate (pH 7.2)], 1×Denharts [1×Denharts=a solution containing 0.2% each of Ficoll, BSA, and polyvinylpyrrolidone], and 100-200 μg of denaturated sheared salmon sperm DNA (S.S. DNA)/ml, 1 mM EDTA, and 0.1% SDS. This treatment will decrease the amount of binding between the filter and non-hybridized probe DNA next to be applied to the filters.

To screen for recombinant plasmids containing HS TK inserts, the transformed colonies fixed to the original, treated, nitrocellulose filters were hybridized with $^{32}P$ labelled Bam HSV TK fragment by immersion of the filters in hybridization buffer containing 2×SSC (pH 7.2), 1× Denhart's solution, 50 μg of S.S. DNA/ml, 1 mM EDTA, 0.1% of SDS, 10% of dextran sulfate, and $^{32}P$ Bam TK as the hybridization probe. The level of radioactivity of the solution was approximately 100,000 counts per minute (cpm) per milliliter.

Hybridization was effected at 60° C. over 18-24 hours [Wahl et al. Proc. Natl. Acad. Sci. USA 76, 3683-3687 (1979)].

[To prepare the hybridization probe, the 2.3 md Bam TK fragment was labelled by nick translation according to the method of Rigby et al., J. Mol. Biol. 113, 237-251 (1977). More specifically, 0.1 ml of a reaction mixture was prepared containing 50 mM Tris-HCl (pH 7.6), 5 mM $MgCl_2$, 20 uM deoxycytidine triphosphate (dCTP), 20 μM deoxyadenosine triphosphate (dATP), 20 μM deoxyguanosine triphosphate (dGTP), 2 μM (alpha-$^{32}P$)deoxythymidine triphosphate (dTTP) (410 Curies/m mol) (Amersham Corporation), 1 ng of DNase I, 100 units of DNA polymerase I (Boehringer Mannheim), and 1 μg of Bam TK fragment. The reaction mixture was incubated at 14° C. for 2 hours. The reaction was terminated by adding 50 ul of 0.5 M EDTA and heating to 65° C. for 10 minutes. Unincorporated triphosphates were removed by gel filtration of the reaction mixture on Sephadex G50.]

After hybridization, excess probe was removed from the nitrocellulose filters by washing 5 times in 2×SSC (pH 7.2) containing 0.1% of SDS at room temperature, followed by 3 washes in 0.2×SSC (pH 7.2) containing 0.1% of SDS at 60° C., with each wash lasting 30 minutes. The washed filters were then air dried and used to expose X-ray film (Kodak X-omat R) at −70° C. for 6-18 hours using a Cronex Lightening Plus intensifying screen (du Pont) for enhancement.

The exposed and developed X-ray film was then used to determine which colonies contained pBR 322 vaccinia Bam HSV TK recombinant plasmids. Those colonies which exposed the X-ray film were located on the corresponding replica nitrocellulose filter. Such positive colonies wer then picked from the replica filters for further analysis. Of the approximately 1000 colonies screened in this manner, 65 colonies were tentatively identified as having a Bam TK insert within pDP 3.

EXAMPLE VII

Restriction Analysis of Recombinant Plasmids Containing Bam HSV TK

Each of the 65 colonies which were tentatively identified as containing recombinant plasmids with Bam HSV TK inserts were used to inoculate 2.0 ml cultures of LB broth containing ampicillin at 100 μg/ml. The cultures were then incubated at 37° C. overnight. Plasmids were extracted from each culture as described in Example III. The plasmids were dissolved in a 50 μl of water after isopropanol precipitation.

To determine if the plasmids contained an intact 2.3 md Bam HSV TK fragment and at which Bam HI site within pDP 3 the Bam HSV TK was inserted, 25 μl of each plasmid preparation were mixed with 25 μl of 2×Hind III buffer and digested at 37° C. for 2 hours with 1 unit of Hind III. The resulting fragments were then analyzed by electrophoresis on a 1.0% agarose gel as described previously.

Of the 65 plasmid preparations analyzed 6 were found to contain Bam HSV TK fragments inserted into the Bam HI site present in the vaccinia Hind III F portion of the plasmid, i.e. they yielded Hind III restriction fragments of molecular weights corresponding to linear pBR 322 (2.8 md) and fragments of a molecular weight greater than that of the vaccinia Hind III F fragment (8.6 md).

These 6 plasmids were further analyzed with Sst I (an isoschizomer of Sac 1) to determine the number and orientation of the Bam HSV TK fragments inserted within vaccinia Hind III F Fragment, since Sst I (Sac I) cleaves both the Bam HSV TK fragment and the vaccinia Hind III F fragment asymetrically. The analyses were performed by mixing 25 μl of the plasmid with 25 μl of 2×Sst buffer [50 mM Tris-HCl (pH 8.0), 10 mM of $MgCl_2$, 100 mM of NaCl, and 10 mM of DTT] and digesting with 1 unit of Sst I (Bethesda Research Laboratories) at 37° C. for 2 hours. The resulting fragments were analyzed by electrophoresis in 1% agarose gels. Of the 6 plasmids analyzed, 5 yielded two Sst I fragments with molecular weights of 10.1 md and 3.5 md, indicating a single Bam HSV TK insert. One of these plasmids was selected for further study and designated pDP 132. The other plasmid yielded three Sst I fragments with molecular weights of 10.8 md, 2.8 md, and 2.3 md, indicating tandom Bam HSV TK inserts oriented head to tail and in the opposite orientation as compared to pDP 132. This plasmid was designated pDP 137. The plasmids pDP 132 and pDP 137 are diagramed in FIG. 3C.

EXAMPLE VIII

Isolation of a TK⁻ S-variant Vaccinia Virus

To isolate a TK⁻ S-variant vaccinia virus mutant, a virus population was subjected to strong selective pressure for such a mutant by growing the virus in cells in the presence of BUdR, which is lethal to organisms carrying the TK gene. More in particular, confluent monolayers of TK⁻ human (line 143) cells growing in Eagle's Special medium in 150 mm Petri dishes were infected with approximately $3 \times 10^3$ plaque forming units (pfu) of S-variant vaccinia virus per dish (20 dishes used) in the presence of 20 ug BUdR/ml. (Eagle's Special medium is a commercially available nutrient medium for the growth of most cell lines. Alternative media such as Eagle's Minimum Essential Medium, Basal Eagle's Medium, Ham's-F10, Medium 199, RPMI-1640, etc., could also be used.) Growth is at 37° C. in an atmosphere enriched in $CO_2$. This is conveniently done using a $CO_2$-incubator providing air enriched with $CO_2$ to have a $CO_2$ content of about 5 percent.

Ninety-three of the plaques which developed were isolated and replaqued on TK⁻ human (line 143) cells under the conditions mentioned previously and again in the presence of 20 μg of BUdR/ml. A number (5) of large, well isolated plaques were picked for further analysis.

The five plaque isolates were tested for growth on cell monolayers under the same conditions used earlier and in the presence or absence of 20 ug BUdR/ml. The relative growth of each plaque in the presence and absence of BUdR was noted and compared with the relative growth in similar monolayer cell cultures of the parent S-variant virus. The following results were obtained:

| Plaque Isolate | −BUdR (pfu/ml) | +BUdR (pfu/ml) |
|---|---|---|
| #70 | $5.1 \times 10^5$ | $4.1 \times 10^5$ |
| #73 | $1.0 \times 10^6$ | $1.0 \times 10^6$ |
| #76 | $4.7 \times 10^5$ | $4.7 \times 10^5$ |
| #79 | $5.4 \times 10^5$ | $4.4 \times 10^5$ |
| #89 | $5.9 \times 10^5$ | $7.0 \times 10^5$ |

| Plaque Isolate | −BUdR (pfu/ml) | +BUdR (pfu/ml) |
|---|---|---|
| S-variant | $1.7 \times 10^{10}$ | $9.7 \times 10^6$ |

The growth of plaque isolate #79 was further monitored in the presence of 0, 20 and 40 ug BUdR/ml and compared with the growth of its parent S-variant virus. The following results were obtained:

| Virus | Yield (pfu/ml) 0 μg/ml | 20 μg/ml | 40 μg/ml |
|---|---|---|---|
| #79 | $2.5 \times 10^5$ | $4.1 \times 10^5$ | $3.2 \times 10^5$ |
| S-Variant | $1.2 \times 10^9$ | $1.3 \times 10^6$ | $2.0 \times 10^5$ |

In addition, the above 5 plaque isolates and the S-variant parent were monitored for growth on TK⁻ human (line 143) cells in the presence of MTAGG. MTAGG is an Eagles's Special medium modified by the presence of:

| | |
|---|---|
| $8 \times 10^{-7}$ M | methotrexate |
| $1.6 \times 10^{-5}$ M | thymidine |
| $5 \times 10^{-5}$ M | adenosine |
| $5 \times 10^{-5}$ M | guanosine |
| $1 \times 10^{-4}$ M | glycine |

(cf. Davis et al., op. cit.) and selects for thymidine kinase and against organisms free of the thymidine kinase gene. The results of such an experiment were as follows:

| Virus | Plaque Forming Units/ml −MTAGG | +MTAGG |
|---|---|---|
| #70 | $4.0 \times 10^5$ | 0 |
| #73 | $5.8 \times 10^5$ | 0 |
| #76 | $2.8 \times 10^5$ | $3.3 \times 10^3$ |
| #79 | $3.6 \times 10^5$ | 0 |
| #80 | $4.3 \times 10^5$ | $4.0 \times 10^3$ |
| S-Variant | $4.8 \times 10^9$ | $2.6 \times 10^9$ |

Of the three plaque isolates showing complete inhibition of growth in the presence of MTAGG, isolate #79 was arbitrarily selected and extracts prepared from cells infected with #79 virus were compared with extracts prepared from uninfected cells and from cells infected with the S-variant parent virus with respect to the ability of the extracts to phosphorylate tritiated ($^3H$) thymidine. The results are tabulated below:

| Extract Source | $^3H$ Thymidine Phosphorylated (cpm/15 μg Protein) |
|---|---|
| Uninfected TK⁻ human (line 143) | 0 |
| #79 infected cells | 90 |
| S-variant infected cells | 66,792 |

In view of (1) resistance to BUdR, (2) inhibition of growth by a medium containing MTAGG, and (3) failure to detect significant phosphorylation of thymidine in infected cell extracts, plaque isolate #79 is considered to lack thymidine kinase activity. The isolate is designated VTK⁻79.

EXAMPLE IX

Marker Rescue of L-variant Vaccinia DNA by the S-Variant

Four preparations of L-variant DNA were prepared for marker rescue studies. The first consisted of purified, intact, L-variant vaccinia DNA. The second consisted of L-variant vaccinia DNA digested with Bst E II, a restriction endonuclease which generates a donor DNA fragment, fragment C, comprising that DNA which is absent from the S-variant and uniquely present in the L-variant and which also has, at both ends of the DNA chain, a region of DNA homologous with corresponding sequences in the S-variant. The third and fourth preparations respectively consisted of L-variant DNA digested with Ava I and Hind III, restriction endonucleases that cleave the vaccinia genome within the unique L-variant DNA sequence. The marker rescue studies performed with these four preparations demonstrate that those L-variant DNA fragments containing the deleted region absent from the S-variant can be reintroduced into the S-variant by an in vivo recombination technique providing that the fragment contains, in addition to the deleted region, terminal regions which are homologous with corresponding sequences in the S-variant.

Figure 6B:
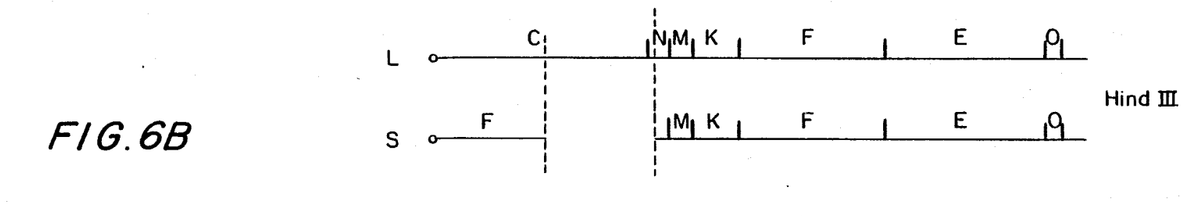
Figure 6C:
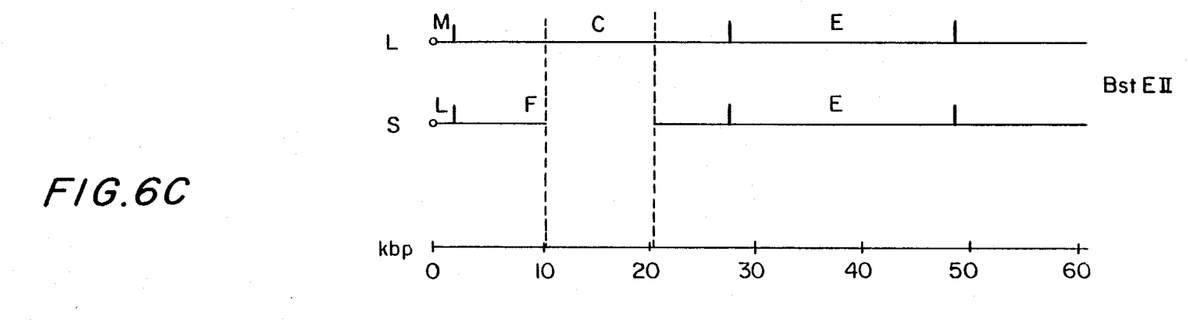

A better understanding of the fragments employed in these studies will be had by referring to FIGS. 6 A-C, each of which is a restriction map of a portion of the left terminus of the vaccinia genome. More in particular, each map refers to the left-terminal region of the genome comprising approximately 60 kilobasepairs, as indicated in the Figure. The portion of the vaccinia genome which is deleted from the S-variant is represented in each map as the region between the dotted lines shown in the Figures, a region approximately 10 kilobasepairs in length.

Turning now more specifically to FIG. 6A, it is evident that fragment H obtained by digestion with Ava I is completely within the deleted region but will have no terminal DNA fragments homologous with the DNA of the S-variant because the Ava I cleavage sites fall entirely within the deleted region of the S-variant.

The restriction map of FIG. 6B pertaining to Hind III shows that this restriction enzyme similarly fails to produce a L-variant DNA fragment overlapping the deleted region of the S-variant. In this instance, sequences homologous with the S-variant are found at the left terminus of the C-fragment of Hind III. However, the restriction site at the right-hand terminus of fragment C falls within the deleted region and there is no terminal sequence homologous with the DNA sequence of the S-variant.

In contrast, the restriction map shown in FIG. 6C pertaining to Bst E II shows that digestion with this enzyme produces a fragment, fragment C, which includes the deleted region absent from the S-variant and also has terminal portions at both the left and right ends which are homologous with corresponding portions of the S-variant.

The results of the experiments, discussed more in detail below, indicate that the DNA which is present in the L-variant but is deleted from the S-variant is rescued by the S-variant with high efficiency from the intact L-variant genome, is rescued with lower efficiency from the C fragment of Bst E II, and cannot be rescued from either of the L-variant DNA fragments prepared with the Ava I and Hind III restriction endonucleases.

The high efficiency with which the deleted sequence is rescued from the intact L-variant is attributable to the fact that a single crossover between the intact L-variant and the S-variant is sufficient to produce an L-variant genome type. On the other hand, to rescue the deleted portion from the C fragment of Bst E II, a crossover between the fragment and the S-variant is necessary in both the left- and right-hand terminal portions of the C-fragment in order to incorporate the deleted region into the S-variant. Finally, since neither digestion with Ava I nor with Hind III produces DNA fragments which can be incorporated into the S-variant by any crossover, no rescue of the deleted portion is effected.

The marker rescue was performed on CV-1 monolayers using the calcium phosphate technique of Graham et al., Virology, 52, 456–467 (1973), as modified by Stow et al. and Wigler et al., both mentioned earlier herein. Confluent CV-1 monolayers were infected with S-variant vaccinia virus to give approximately 50 to 200 plaques in each of a number (5–20) of Petri-dishes of 6 cm diameter. To infect the cells, the growth medium (e.g. Eagle's Special containing 10% calf serum) is aspirated and a dilution of the virus containing 50–200 pfu/0.2 ml in a cell-compatible medium such as Eagle's Special containing 2% calf serum is applied to the cell monolayer. After incubation for a period of one hour at 37° C. in a $CO_2$-incubator to permit the absorption of the virus to the cells, various of the four L-variant DNA preparations earlier mentioned were each separately added to the monolayers as a calcium phosphate precipitate containing one microgram per dish of the L-variant DNA preparation. After 40 minutes, Eagle's Special medium with 10% calf serum was added and, four hours after the initial addition of the DNA, the cell monolayer was exposed to 1 ml of buffered 25 percent dimethyl sulfoxide for four minutes. This buffer contains 8 g of NaCl, 0.37 g of KCl, 0.125 g of $Na_2HPO_4.2-H_2O$, 1 g of dextrose, and 5 g of N-(2-hydroxyethyl)-piperazine,N'-(2-ethanesulfonic acid) (Hepes) per liter, having a final pH of 7.05. The dimethylsulfoxide was removed and the monolayers were washed and overlayed with nutrient agar. After three days, at 37° C. in a $CO_2$-incubator, the cells were stained with a nutrient agar overlay containing Neutral red dye, which stains the uninfected cells (nutrient agar=Eagle's Special medium containing 10% calf serum and 1% agar). The next day, the agar overlay was removed and the monolayers were transferred to nitrocellulose filters and prepared for in situ hybridization as described by Villarreal et al., loc. cit. Since digestion of the L-variant genome with Ava I generates a 6.8 kilobasepair fragment, fragment H, that resides entirely with the unique DNA sequences deleted in the S-variant genome (cf. FIG. 6A), $^{32}P$-labelled nick-translated Ava I H fragment provides a highly specific probe for detecting the rescue of the unique L-variant DNA sequence by the S-variant.

For hybridization, the nitrocellulose filters were interleaved with Whatman No. 1 filter paper circles in 6 cm Petri dishes and wer prehybridized for 6 hours at 60° C. in prehybridization buffer (SSC Denhardt solution, EDTA, and S.S.DNA) as described earlier herein in Example VI. The radioactive probe consisting of $^{32}P$-labelled nick-translated L-variant Ava I, H fragment, having a specific activity of approximately $1 \times 10^8$ cpm/μg was used for hybridization in $2 \times SSC$, $1 \times Den$- hardt, 1 mM EDTA, 0.1 percent SDS, 10 percent of dextran sulfate, and 50 μg/ml of sonicated S.S.DNA at approximately $1 \times 10^5$ cpm/ml overnight at 60° C. The radioactive probe was prepared according to the method of Rigby et al., J. Mol. Biol. 113, 237-251 (1977). The filters were washed repeatedly at room temperature and at 60° C. using the washing procedure of Example VI, were air dried, and radioautographed.

The results of the experiments are summarized in Table I below:

TABLE I

| Donor L-variant DNA Preparation | Percent of Plaques Containing L-variant Genotype |
|---|---|
| Intact L-variant | 5 |
| Bst E II total digest | 0.1 |
| Ava I total digest | 0 |
| Hind III total digest | 0 |

A minimum of 5000 plaques were analyzed for each donor DN preparation.

EXAMPLE X

In vivo Recombination Using pDP 132 and pDP 137 to Generate Vaccinia Virus Mutants VP-1 through VP-6 and Identification Thereof Using Replica Filters A first calcium orthophosphate precipitate of donor DNA was prepared by combining 5 μg of pDP 132 Hind III digested DNA in 50 μl of water, 4 μg of S-variant carrier DNA (prepared as in Example I) in 40 μl of water, and 10 μl of 2.5M $CaCl_2$, combining the resultant mixture with an equal volume of 2×Hepes phosphate buffer comprising 280 mM NaCl, 50 mM Hepes, and 1.5 mM sodium phosphate (pH=7.1), and permitting the precipitate to form over a period of 30 minutes at room temperature. A second precipitate was prepared in the same fashion, in the same amounts, but using pDP 137 Hind III digested DNA.

[As described more in detail by Stow et al. loc. cit. and Wigler et al., loc. cit., the modifications of the Graham et al. precipitation technique referred to earlier employ carrier DNA as high molecular weight substance increasing the efficiency of calcium orthophosphate precipitate formation. The carrier DNA employed is DNA from the virus which is used for infection of the monolayered cells in the in vivo recombination technique.]

For in vivo recombination, confluent monolayers of CV-1 growing in Eagle's Special medium containing 10% calf serum were infected with S-variant vaccinia virus at a multiplicity of infection of 1 pfu/cell. The infection procedure is like that described in Example IX. The virus was permitted to absorb for 60 minutes at 37° C. in a $CO_2$-incubator, after which the innoculum was aspirated and the cell monolayer was washed. The precipitated DNA preparations were applied to separate cell monolayers and, after 40 minutes at 37° C. in a $CO_2$-incubator, liquid overlay medium was added (Eagle's Special containing 10% calf serum). In each case, the virus was harvested after 24 hours at 37° C. in a $CO_2$-incubator by 3 freeze/thaw cycles and titered on CV-1 monolayers. Approximately 15,000 plaques were analyzed on CV-1 monolayers for recombinant virus using replica filters prepared as follows.

Plaques formed on confluent CV-1 monolayers under a nutrient agar overlay were transferred to a nitrocellulose filter by removing the agar overlay cleanly with a scalpel and placing the nitrocellulose filter onto the monolayer. Good contact between the filter and monolayer was effected by placing a Whatman No. 3 filter paper, wetted in 50 mM Tris buffer (pH=7.4) and 0.015 mM NaCl over the nitrocellulose filter and tamping with a rubber stopper until the monolayer transferred to the nitrocellulose shows a uniform color surrounding discrete uncolored plaques. (The monolayer has been previously stained with Neutral red, which is taken up by viable cells, i.e. cells unlysed by virus infection).

The nitrocellulose filter having the transferred monolayer thereon is now removed from the Petri dish and placed with the monolayer side up. A second nitrocellulose filter, wetted in the above-mentioned Tris-NaCl solution, is now placed directly over the first nitrocellulose filter and the two filters are brought firmly into contact by tamping with a rubber stopper after protecting the filters with a dry Whatman No. 3 circle. After removing the filter paper, the nitrocellulose filters are notched for orientation and separated. The second (replica) nitrocellulose filter now contains a mirror image of the cell monolayer transferred to the first nitrocellulose filter. The second filter is conveniently placed in a clean Petri dish and frozen. The first nitrocellulose filter is subjected to hybridization employing $^{32}P$-labelled Bam HSV TK fragment as a probe. The preparation of the probe and the hybridization technique are described earlier herein in Example VI.

Approximately 0.5 percent of the plaques analyzed by hybridization were positive, i.e. were recombinant virus containing Bam HSV TK.

Plaques of recombinant virus corresponding to those identified on the first nitrocellulose filter by hybridization were then isolated from the nitrocellulose replica filter by the following technique for further purification.

Using a sharp cork borer having a diameter slightly larger than the plaque to be picked, a desired plaque is punched out from the first or original nitrocellulose filter which has been used for identification of recombinants by hybridization. The resulting perforated filter is next used as stencil to identify and isolate the corresponding plaque on the replica filter. Namely, the replica filter is placed with the monolayer side up on a sterile surface and covered with a sheet of Saran wrap. The perforated first or original nitrocellulose filter is then placed monolayer side down over the second filter and the orientation notches present in the filters are aligned to bring the mirror images of the plaques into register. Again, using a cork borer, a plug is removed from the replica filter and, after removal of the Saran wrap protective layer, is placed in one ml of Eagle's Special medium containing 2% calf serum. The nitrocellulose plug is sonicated in this medium for 30 seconds on ice to release the virus. 0.2 ml of this virus preparation, and 0.2 ml of a 1:10 dilution of the preparation, are plated on CV-1 monolayers present in 6 cm Petri dishes.

As a plaque purification step, the entire sequence of preparing a first nitrocellulose filter, a replica filter, hybridization, and plaque isolation from the replica filter was repeated.

One sample of a purified plaque prepared in this manner starting from a calcium orthophosphate precipitate of pDP 132 Hind III digested DNA was denominated vaccinia virus VP-1. Similarly, a plaque containing a recombinant prepared from pDP-137 Hind III digested DNA was denominated VP-2. Both samples were grown up on suitable cell cultures for further study, including identification by restriction analysis and other techniques.

In like fashion, two further vaccinia mutants respectively denominated VP-3 and VP-4 were prepared by in vivo recombination employing VTK-79 (an S-variant TK⁻ vaccinia virus as described in Example VIII) as the rescuing virus and, respectively, pDP 132 and pDP 137 as the plasmid donor DNA. The precipitates were formed as described earlier herein except that 5 $\mu$g of plasmid donor DNA present in 50 $\mu$l of water, 4 $\mu$g of VTK−79 carrier DNA in 150 $\mu$l of water, and 50 $\mu$l of 2.5M $CaCl_2$ were combined and added dropwise to an equal volume of 250 $\mu$l of the Hepes phosphate buffer earlier described.

Further, the cells employed for infection by the VTK−79 virus carrier were BHK-21 (Clone 13) cells instead of CV-1.

Two further vaccinia virus mutants denominated VP-5 and VP-6 were prepared using calcium orthophosphate precipitates of pDP 132 and pDP 137, respectively, each as prepared for mutants VP-3 and VP-4. However, in the case of mutants VP-5 and VP-6, the carrier DNA is vaccinia virus VTK−11, rather than VTK −79.

Again, BHK-21 (C-13) cell monolayers were infected, the rescuing virus in this case being VTK−11.

EXAMPLE XI

Expression of HSV TK by Vaccinia Mutant VP-2 and the Use of IDC* for Identification Thereof The virus product obtained in Example X by the in vivo recombination of S-variant vaccinia virus and the calcium orthophosphate precipitate of pDP-137 Hind II digested DNA was plated out on confluent monolayers of CV-1 cells present on approximately twenty 6 cm Petri dishes at a concentration giving approximately 150 plaques per dish. The plaques were covered with a liquid overlay medium, e.g. Eagle's Special medium containing 10% calf serum. After 24 to 48 hours of incubation at 37° C. in a $CO_2$-incubator, the liquid overlay medium was removed from the dishes and replenished in each case with 1.5 ml of the same liquid overlay medium containing 1-10 $\mu$Ci of $^{125}I$ iododeoxycytidine (IDC*). The plates were then further incubated overnight, at 37° C. in an enriched $CO_2$ atmosphere, after which the cell monolayer present thereon was stained by the addition of Neutral red to visualize the plaques by contrast.

The medium was then removed by aspiration, the monolayers were washed three times with phosphate-buffered saline solution, and the cell monolayer on each of the plates was imprinted onto a corresponding nitrocellulose filter. The latter was exposed to X-ray film for from 1 to 3 days and then developed.

Those viral plaques containing and expressing the HSV TK gene will phosphorylate IDC* and incorporate it into their DNA, rendering the DNA insoluble. Other, unphosphorylated and unincorporated, IDC* was removed by washing, so that plaques darkening the X-ray film are those expressing recombinant HSV TK gene. Neither CV-1 cells nor vaccinia, although containing TK, will phosphorylate and incorporate IDC* in the selective fashion characteristic of the HSV TK.

After the recombinant organisms has been identified by radioautography, filter plugs were cut from the nitrocellulose filter, placed in 1 ml of overlay medium, (Eagle's Special, 10% calf serum), sonicated, and replated on CV-1 monolayers. The IDC* assay was then repeated further to purify the viral isolates. In this manner, a virus identical to the VP-2 mutant identified by hybridization in Example X was isolated by a technique dependent on the expression of the HSV TK gene present therein.

Again, the results of this Example demonstrate the expression of the HSV TK gene, present in the recombinant organisms according to the present invention by certain of those organisms.

Those vaccinia mutants derived from pDP 137, namely VP-2, VP-4, and VP-6, all will express the HSV TK gene present therein by phosphorylation and incorporation of IDC* in the manner described above. However, the variants VP-1, VP-3, and VP-5, derived from pDP 132, will not so express the gene, possibly because the orientation of the gene within the virus is contrary to the direction of gene transcription.

EXAMPLE XII

The use of a Selective Medium for the Identification and Isolation of Recombinant Virus Containing HSV TK Gene Viruses prepared according to Example X by the in vivo recombination, in BHK-21 (C-13) cells, of VTK−79 vaccinia virus and a calcium orthophosphate precipitate of pDP 137 were used to infect human (line 143) TK⁻cells. More in particular, cell monolayers, in five Petri dishes 6 cm in diameter, were each infected with the virus of Example X at a dilution of the virus from $10^0$ to $10^{-4}$ in the presence of selective MTAGG medium. The infection technique was as described earlier.

Five well-separated plaques were isolated and one was replated on CV-1 monolayers for a second cycle of plaque purification. One further well-separated plaque, purified twice by plaque purification, was chosen and analyzed. A well-isolated plaque, thus twice plaque-purified, was selected and analyzed for the presence of the HSV TK gene by in situ hybridization employing $^{32}P$-labelled Bam HSV TK. The hybridization technique was, again, as described earlier. The mutant vaccinia virus, positive for the presence of the HSV TK gene, was denominated VP-4.

What is claimed is:

1. A method for the in vivo recombination of vaccinia virus DNA with DNA not naturally occurring in vaccinia virus, which method comprises infecting a cell with vaccinia virus in a cell-compatible medium in the presence of doner DNA, said donor DNA comprising said DNA not naturally occurring in vaccinia virus flanked by DNA sequences homologous with portions of the vaccinia genome, whereby said DNA not naturally occurring in vaccinia is introduced into the genome of said vaccinia virus, and then recovering vaccinia virus modified by such in vivo recombination.

2. A method as in claim 1 wherein said flanking DNA sequences are co-linear with portions of the genome of the vaccinia virus except for the presence of said DNA not naturally occurring in vaccinia virus.

3. A method as in claim 1 wherein said flanking sequences are co-linear with portions of the genome of the vaccinia virus in a non-essential region thereof, except for the presence of said DNA not naturally occurring in vaccinia virus.

4. A method for the in vivo recombination of vaccinia virus DNA and DNA not naturally occurring in vaccinia virus, which method comprises infecting a cell with vaccinia virus in a cell-compatible medium in the presence of donor DNA, said donor DNA comprising said DNA not naturally occurring in vaccinia virus present within a segment of vaccinia DNA, whereby said DNA not naturally occurring in vaccinia is introduced into the genome of said vaccinia virus, and then recovering vaccinia virus modified by such in vivo recombination.

5. A method as in claim 4 wherein said segment of vaccinia DNA is co-linear with portions of the vaccinia genome except for the presence of said DNA not naturally occurring in vaccinia virus.

6. A method as in claim 5 wherein said DNA not naturally occurring in vaccinia virus is present within a non-essential region of said segment of vaccinia DNA.

7. A method as in claim 5 wherein said cell is present in a cell monolayer.

8. A method for the in vivo recombination of vaccinia virus DNA with DNA not naturally occurring in vaccinia virus, which method comprises contacting a cell monolayer with a cell-compatible medium containing vaccinia virus and with a cell-compatible medium comprising donor DNA, said donor DNA comprising said DNA not naturally occurring in vaccinia virus present within a non-essential region of a segment of vaccinia virus otherwise co-linear with portions of the vaccinia genome, whereby said DNA not naturally occurring in vaccinia is introduced into the genome of said vaccinia virus, and then recovering vaccinia virus modified by such in vivo recombination.

9. A method as in claim 8 wherein said donor DNA is clonable with a plasmid.

10. A method as in claim 8 wherein said DNA not naturally occurring in vaccinia virus comprises the Bam HI TK gene of herpes simplex.

11. A method as in claim 8 wherein said co-linear segment of vaccinia DNA is the Hind III F-fragment thereof.

12. A method as in claim 8 wherein said donor DNA is present as a calcium orthophosphate precipitate of said donor DNA.

13. A method as in claim 8 wherein said vaccinia virus is free of a vaccinia gene producing thymidine kinase.

14. The method of replicating DNA in a eukaryotic cell by infecting said cell with a vaccinia virus modified to contain said DNA, said DNA not naturally occurring in vaccinia virus.

15. A method as in claim 14 wherein said DNA is also not naturally occurring in said cell.

16. A method as in claim 14 wherein said DNA is expressed by said cell.

17. A method as in claim 15 wherein said DNA is expressed by said cell.

18. A method as in claim 16 wherein said DNA is expressed by the production by said cell of a biologically active protein.

19. A method as in claim 17 wherein said DNA is expressed by the production by said cell of a biolgically active protein.

* * * * *